US009789463B2

(12) United States Patent
Kufeld et al.

(10) Patent No.: US 9,789,463 B2
(45) Date of Patent: Oct. 17, 2017

(54) HEAT TRANSFER IN A POLYMERIZATION REACTOR

(71) Applicant: Chevron Phillips Chemical Company LP, The Woodlands, TX (US)

(72) Inventors: Scott E. Kufeld, Houston, TX (US); Joel A. Mutchler, Kingwood, TX (US); John D. Hottovy, Porter, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 723 days.

(21) Appl. No.: 14/313,370

(22) Filed: Jun. 24, 2014

(65) Prior Publication Data

US 2015/0367319 A1 Dec. 24, 2015

(51) Int. Cl.
| | | |
|---|---|---|
| *C08F 2/00* | (2006.01) | |
| *B01J 19/18* | (2006.01) | |
| *G06F 17/50* | (2006.01) | |
| *B01J 19/24* | (2006.01) | |
| *C08F 2/01* | (2006.01) | |
| *G06F 19/00* | (2011.01) | |
| *C08F 2/12* | (2006.01) | |
| *C08F 2/18* | (2006.01) | |

(52) U.S. Cl.
CPC ......... *B01J 19/2435* (2013.01); *B01J 19/245* (2013.01); *C08F 2/01* (2013.01); *C08F 2/12* (2013.01); *C08F 2/18* (2013.01); *G06F 17/50* (2013.01); *G06F 19/701* (2013.01); *B01J 2219/00051* (2013.01); *B01J 2219/00094* (2013.01)

(58) Field of Classification Search
CPC ....... C08F 2/12; C08F 2/18; C08F 2/01; B01J 19/2435; B01J 19/245; B01J 2219/00094; B01J 2219/00051; G06F 17/50
USPC ................................ 703/1; 422/132; 526/64
See application file for complete search history.

(56) References Cited

U.S. PATENT DOCUMENTS

| | | | |
|---|---|---|---|
| 3,248,179 | A | 4/1966 | Norwood |
| 4,501,885 | A | 2/1985 | Sherk et al. |
| 4,588,790 | A | 5/1986 | Jenkins, III et al. |
| 5,352,749 | A | 10/1994 | DeChellis et al. |
| 5,436,304 | A | 7/1995 | Griffin et al. |

(Continued)

FOREIGN PATENT DOCUMENTS

EP 0479186 4/1992

OTHER PUBLICATIONS

International Application No. PCT/US2015/036671 Search Report dated Nov. 23, 2015.

(Continued)

*Primary Examiner* — William Cheung
(74) *Attorney, Agent, or Firm* — Conley Rose, P.C.; Rodney B. Carroll; Monte R. Rhodes

(57) ABSTRACT

A process comprises polymerizing an olefin monomer in a loop reactor in the presence of a catalyst and a diluent, and producing a slurry comprising solid particulate olefin polymer and diluent. The Biot number is maintained at or below about 3.0 within the loop reactor during the polymerizing process. The slurry in the loop reactor forms a slurry film having a film coefficient along an inner surface of the reactor wall, and the film coefficient is less than about 500 $BTU \cdot hr^{-1} \cdot ft^{-2} \cdot °F.^{-1}$.

16 Claims, 4 Drawing Sheets

(56) References Cited

U.S. PATENT DOCUMENTS

| | | | |
|---|---|---|---|
| 5,455,314 A | * | 10/1995 | Burns .................. B01J 19/0006 526/61 |
| 5,565,175 A | | 10/1996 | Hottovy et al. |
| 5,575,979 A | | 11/1996 | Hanson |
| 6,239,235 B1 | | 5/2001 | Hottovy et al. |
| 6,262,191 B1 | | 7/2001 | Hottovy et al. |
| 6,833,415 B2 | | 12/2004 | Kendrick et al. |
| 7,163,906 B2 | | 1/2007 | McDaniel et al. |
| 7,473,743 B2 | | 1/2009 | Fouarge et al. |
| 7,619,047 B2 | | 11/2009 | Yang et al. |
| 7,790,820 B2 | | 9/2010 | Jensen et al. |
| 7,960,487 B2 | | 6/2011 | Yang et al. |
| 8,128,877 B2 | | 3/2012 | McElvain et al. |
| 2009/0004417 A1 | | 1/2009 | Follestad et al. |

OTHER PUBLICATIONS

"ASTM A516 Grade 70 and ASME SA516 Grade 70 Carbon Steel Plate for Boilers and Pressure Vessels by Masteel," http://www.azom.com/article.aspx?ArticleID=4787, updated on May 13, 2014, 2 pages, Masteel UK Ltd.

\* cited by examiner

HEAT TRANSFER IN A POLYMERIZATION REACTOR

CROSS-REFERENCE TO RELATED APPLICATIONS

Not Applicable.

STATEMENT REGARDING FEDERALLY SPONSORED RESEARCH OR DEVELOPMENT

Not applicable.

REFERENCE TO A MICROFICHE APPENDIX

Not applicable.

FIELD

This disclosure relates to the heat transfer in a polymerization reactor system.

BACKGROUND

Polyolefins such as polyethylene and polypropylene may be prepared by slurry polymerization. In this technique, feed materials such as diluent, monomer and catalyst are introduced to a loop reaction zone, forming a slurry in the reaction zone. In continuous loop reactors, the slurry circulates through the loop reaction zone, and the monomer reacts with the catalyst in a polymerization reaction. The polymerization reaction yields solid polyolefins in the slurry. A polymerization product having solid polyolefins is then transferred from the reactor and separated to recover the solid polyolefins.

In general, the polymerization process is exothermic, and the heat generated must be removed from the reactor to prevent the polyolefins from melting within the reactor. Such overheating may result in fouling, plugging, or other adverse effects within the reactor. In addition to limiting the adverse effects, maintaining a controlled temperature within the reactor may be important to producing a product having the desired properties.

SUMMARY

In an embodiment, a process comprises polymerizing an olefin monomer in a loop reactor in the presence of a catalyst and a diluent, and producing a slurry comprising solid particulate olefin polymer and diluent. The Biot number is maintained at or below about 3.0 within the loop reactor during the polymerizing. The slurry in the loop reactor forms a slurry film having a film coefficient along an inner surface of the shell, and the film coefficient is less than about 500 BTU·hr$^{-1}$·ft$^{-2}$·° F.$^{-1}$. The Biot number may be maintained at or below about 2.0 within the loop reactor during the polymerizing, the Biot number may be maintained at or below about 1.5 within the loop reactor during the polymerizing, and/or the Biot number may be maintained at or below about 1.1 within the loop reactor during the polymerizing. The slurry may comprise a solids concentration in the range of about 25 wt % to about 70 wt %, the slurry may comprise a solids concentration in the range of about 40 wt % to about 60 wt %, and/or the slurry may comprise a solids concentration greater than about 50 wt %. The loop reactor comprises a shell having a thickness and a thermal conductivity. A ratio of the film coefficient to the thermal conductivity may be in a range of from about 8.0 ft$^{-1}$ to about 50 ft$^{-1}$, and/or a ratio of the film coefficient to the thermal conductivity may be in a range of from about 14 ft$^{-1}$ to about 35 ft$^{-1}$. A ratio of the film coefficient to the thickness may be in a range of from about 1,400 BTU·hr$^{-1}$·ft$^{-3}$·° F.$^{-1}$ to about 240,000 BTU·hr$^{-1}$·ft$^{-3}$·° F.$^{-1}$, and/or a ratio of the film coefficient to the thickness may be in a range of from about 2,400 BTU·hr$^{-1}$·ft$^{-3}$·° F.$^{-1}$ to about 100,000 BTU·hr$^{-1}$·ft$^{-3}$·° F.$^{-1}$. A ratio of the thermal conductivity to the thickness may be in a range of from about 100 BTU·hr$^{-1}$·ft$^{-2}$·° F.$^{-1}$ to about 10,000 BTU·hr$^{-1}$·ft$^{-2}$·° F.$^{-1}$, and/or a ratio of the thermal conductivity to the thickness is in a range of from about 120 BTU·hr$^{-1}$·ft$^{-2}$·° F.$^{-1}$ to about 4,000 BTU·hr$^{-1}$·ft$^{-2}$·° F.$^{-1}$. The shell may comprise a steel selected from the group consisting of: A106 Gr 8 (60), A516 Gr 70, A537 Cl 2, A106 Gr C (40), A202 Gr 8, A285 Gr C, A514 Gr 8, A515 Gr 70, A517 Gr A, A517 Gr 8, A533 Ty A C13, A542 Ty A C12, A678 Gr C, AISI 1010, AISI 1015, MIL-S 24645, and any combination thereof. The shell has a diameter in the range of about 20 inches to about 36 inches. The inner surface of the shell has a surface smoothness of less than 100 RMS, the inner surface of the shell has a surface smoothness of less than 30 RMS, and/or the inner surface of the shell has a surface smoothness of between about 10 RMS and about 30 RMS. The process may also include circulating the slurry within the loop reactor. The slurry may be circulated at a velocity in the range of about 25 ft/s to about 60 ft/s, the slurry may be circulated at a velocity in the range of about 35 ft/s to about 50 ft/s, and/or the slurry may be circulated at a velocity greater than about 40 ft/s.

In another embodiment, a reactor comprises a continuous tubular shell comprising a thickness and a thermal conductivity, and a slurry disposed within the continuous tubular shell. The continuous tubular shell defines a continuous loop and a ratio of the thermal conductivity to the thickness is greater than or equal to about 120 BTU·hr$^{-1}$·ft$^{-2}$·° F.$^{-1}$. The slurry comprises solid particulate olefin polymer and a diluent, and the volume fraction of the solids in the slurry is greater than about 0.65. The ratio of the thermal conductivity to the thickness may be greater than or equal to about 160 BTU·hr$^{-1}$·ft$^{-2}$·° F.$^{-1}$, the ratio of the thermal conductivity to the thickness may be greater than or equal to about 250 BTU·hr$^{-1}$·ft$^{-2}$·° F.$^{-1}$, and/or the ratio of the thermal conductivity to the thickness may be greater than or equal to about 300 BTU·hr$^{-1}$·ft$^{-2}$·° F.$^{-1}$. The thermal conductivity of the shell may be between about 20 and about 40 BTU·hr$^{-1}$·ft$^{-2}$·° F.$^{-1}$. The shell may comprise a steel selected from the group consisting of: A106 Gr 8 (60), A516 Gr 70, A537 Cl 2, A106 Gr C (40), A202 Gr 8, A285 Gr C, A514 Gr 8, A515 Gr 70, A517 Gr A, A517 Gr 8, A533 Ty A C13, A542 Ty A C12, A678 Gr C, AISI 1010, AISI 1015, MIL-S 24645, and any combination thereof. The shell may comprise a steel comprising iron and one or more of components selected from the group consisting of: carbon in an amount of from about 0.05 wt % to about 0.25 wt %, silicon in an amount of from about 0.5 wt % to about 0.75 wt %, manganese in an amount of from about 0.8 wt % to about 2.0 wt %, phosphorous in an amount of from about 0.01 wt % to about 0.1 wt %, sulfur in an amount of from about 0.01 wt % to about 0.1 wt %, aluminum in an amount of from about 0.01 wt % to about 0.04 wt %, chromium in an amount of from about 0.1 wt % to about 0.5 wt %, copper in an amount of from about 0.1 wt % to about 0.5 wt %, nickel in an amount of from about 0.1 wt % to about 0.5 wt %, molybdenum in an amount of from about 0.05 wt % to about 0.1 wt %, niobium in an amount of from about 0.005 wt % to about 0.02 wt %, titanium in an amount of from about 0.01 wt % to about 0.05 wt %, vanadium in an amount of from about 0.01 wt % to about 0.04 wt %, and any combination thereof.

In another embodiment, a process comprises polymerizing an olefin monomer in a loop reactor in the presence of a catalyst and a diluent, where the loop reactor comprises a continuous tubular shell, producing a slurry comprising solid particulate olefin polymer and diluent, and circulating the slurry in the loop reactor. The slurry in the loop reactor forms a slurry film along an inner surface of the shell, and a ratio of a heat transfer resistance through the slurry film to a heat transfer resistance through the tubular shell is maintained at or below about 3.0 within the loop reactor during the polymerizing. The slurry has a velocity of greater than about 30 ft/s during the circulating. The ratio of the heat transfer resistance through the slurry film to the heat transfer resistance through the tubular shell may be maintained at or below about 2.0 within the loop reactor during the polymerizing, and/or the ratio of the heat transfer resistance through the slurry film to the heat transfer resistance through the tubular shell may be maintained at or below about 1.5 within the loop reactor during the polymerizing. The slurry may comprise a solids concentration in the range of about 25 wt % to about 70 wt %. The slurry may comprise a solids volume fraction above about 0.65. The slurry may be circulated at a velocity greater than about 40 ft/s, and/or the slurry is circulated at a velocity greater than about 50 ft/s.

In another embodiment, a polymerization process comprises polymerizing an olefin monomer in a loop reactor in the presence of a catalyst and a diluent, producing a slurry comprising solid particulate olefin polymer and diluent within the loop reactor, and contacting at least a portion of an exterior surface of the loop reactor with a coolant fluid. The slurry in the loop reactor forms a slurry film having a film coefficient along an inner surface of the loop reactor, and the coolant fluid forms a coolant film having a coolant film coefficient along an exterior surface of the loop reactor. A ratio of the film coefficient to the coolant film coefficient is greater than about 2.0. An external Biot number may be greater than about 2.0 during the polymerizing, and/or an internal Biot number may be less than about 3.0 during the polymerizing. The slurry comprises a solids volume fraction above about 0.65. The polymerization process may also include circulating the slurry in the loop reactor, and the slurry may have a velocity of greater than about 30 ft/s during the circulating.

In another embodiment, a method of designing a loop slurry polymerization reactor comprises simulating, on a processor, a loop slurry polymerization reactor, determining a Biot number of a shell region of the at least one loop slurry polymerization reactor based on the simulating, adjusting a value of at least one design parameter for the loop slurry polymerization reactor based on the simulating, repeating the simulating, by the processor, based on the adjusted value of the at least one design parameter, determining that one or more predetermined design parameters are obtained based on the repeating, and outputting a loop slurry polymerization reactor design based on the simulating, adjusting, repeating, and determining. The loop slurry polymerization reactor comprises at least one loop reactor and at least one cooling jacket, and an annulus exists between a wall of the at least one loop reactor and the cooling jacket. The method may also include graphically displaying at least a portion of the simulating, and adjusting the value of the at least one design parameter in response to the graphically displaying. The method may also include determining a position of the at least one cooling jacket adjacent and substantially parallel to at least a portion of a leg of the at least one loop reactor. The at least one design parameter for the loop slurry polymerization reactor may comprise a thermal conductivity of the wall of the at least one loop reactor, a diameter of a wall, a thickness of the wall, a velocity of a slurry within the at least one loop reactor, a slurry density of the slurry, a viscosity of the slurry, a specific heat capacity of the slurry, a thermal conductivity of the slurry, a location of the at least one cooling jacket relative to the wall, or any combination thereof. The one or more predetermined design parameters may comprise a wall thickness. The one or more predetermined design parameters may comprise an internal Biot number equal to or less than about 3.0. A slurry in the at least one loop reactor may form a slurry film having a film coefficient along an inner surface of a wall of the at least one loop reactor, and the one or more predetermined design parameters may comprise the film coefficient of less than about 500 BTU·hr$^{-1}$·ft$^{-2}$·°F.$^{-1}$. A wall of the at least one loop reactor may comprise a thickness and a thermal conductivity, and the one or more predetermined design parameters may comprise a ratio of the thermal conductivity to the thickness that is greater than or equal to about 120 BTU·hr$^{-1}$·ft$^{-2}$·°F.$^{-1}$. The at least one loop reactor may comprise a slurry disposed within a wall of the at least one loop reactor, the slurry may comprise solid particulate olefin polymer and a diluent, and the one or more predetermined design parameters may comprise a volume fraction of the solid particulate olefin polymer in the slurry that is greater than about 0.65.

These and other features will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION OF THE EMBODIMENTS

Disclosed herein are embodiments of a polymerization reactor system and a process for operating the polymerization reactor system under certain heat transfer conditions.

Figure 1:
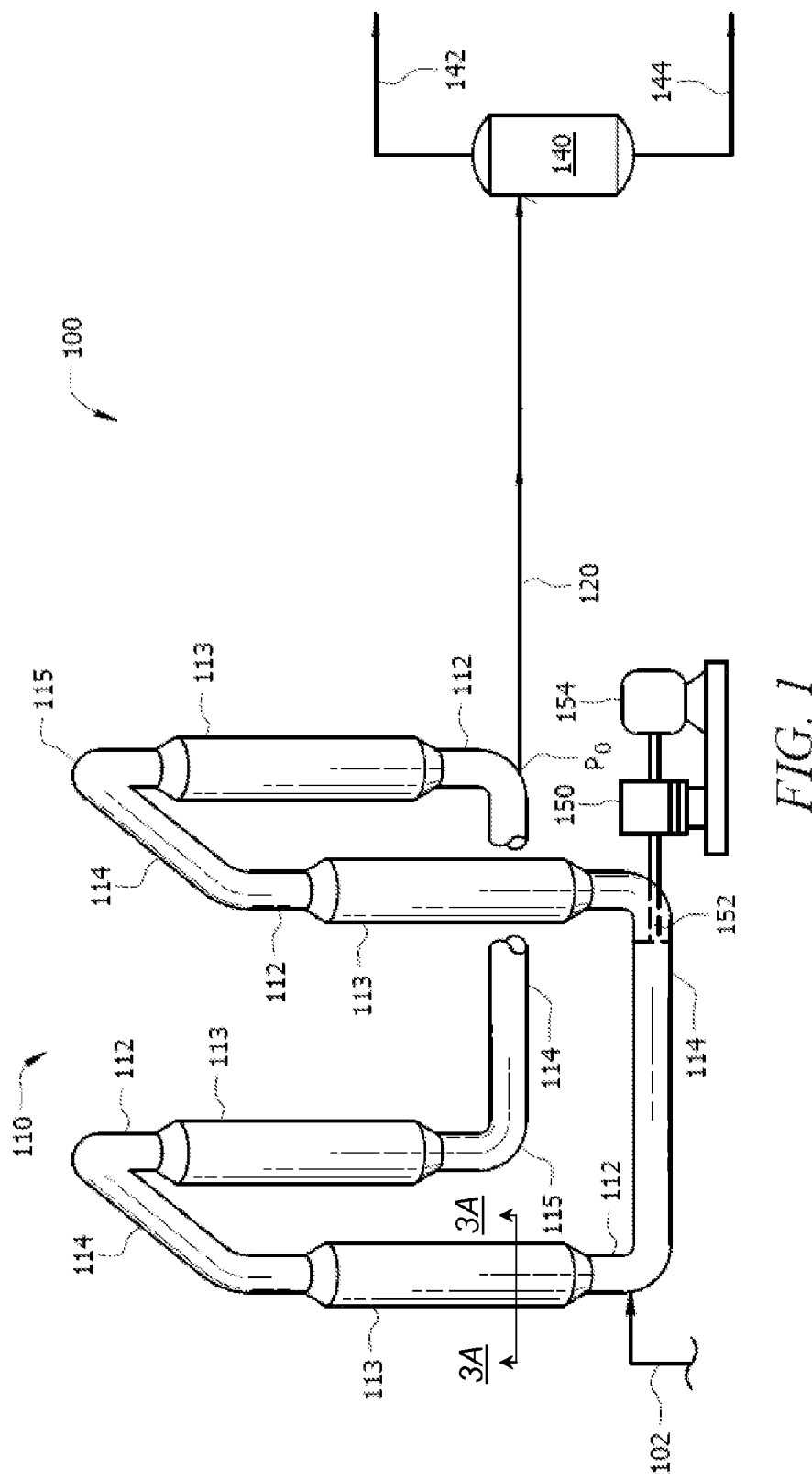
FIG. 1 schematically illustrates a process flow diagram of an embodiment of a loop polymerization process.

FIG. 1 illustrates a schematic process flow diagram of an embodiment of a polymerization system 100. The system 100 may comprise a loop slurry polymerization reactor 110 which forms polymerization product, a first line 120, which receives a polymerization product (e.g., a polymerization product slurry) from the loop slurry polymerization reactor 110, and a separation vessel 140, which receives the polymerization product (e.g., as the polymerization product slurry) from the first line 120. Solid polymer may be recovered from the separation vessel 140.

As disclosed above, the system 100 may comprise a loop slurry polymerization reactor 110. In one or more of the embodiments disclosed herein, the reactor 110 may comprise any vessel or combination of vessels suitably configured to provide an environment for a chemical reaction (e.g., a contact zone) between monomers (e.g., ethylene) and/or polymers (e.g., an "active" or growing polymer chain), and optionally comonomers (e.g., 1-butene, 1-hexene) and/or copolymers, in the presence of a catalyst to yield a polymer (e.g., a polyethylene polymer) and/or copolymer. Although the embodiment illustrated in FIG. 1 shows a single reactor 110, one of skill in the art viewing this disclosure will recognize that any suitable number and/or configuration of reactors may be employed, as described in more detail herein.

As used herein, the terms "polymerization reactor" or "reactor" may include at least one loop slurry polymerization reactor capable of polymerizing olefin monomers or comonomers to produce homopolymers or copolymers. Such homopolymers and copolymers may be referred to as resins or polymers.

The polymerization processes performed in the reactor(s) (e.g., reactor 110) may include batch or continuous processes. Continuous processes could use intermittent or continuous product discharge. Processes may also include partial or full direct recycle of unreacted monomer, unreacted comonomer, and/or diluent.

Figure 2:
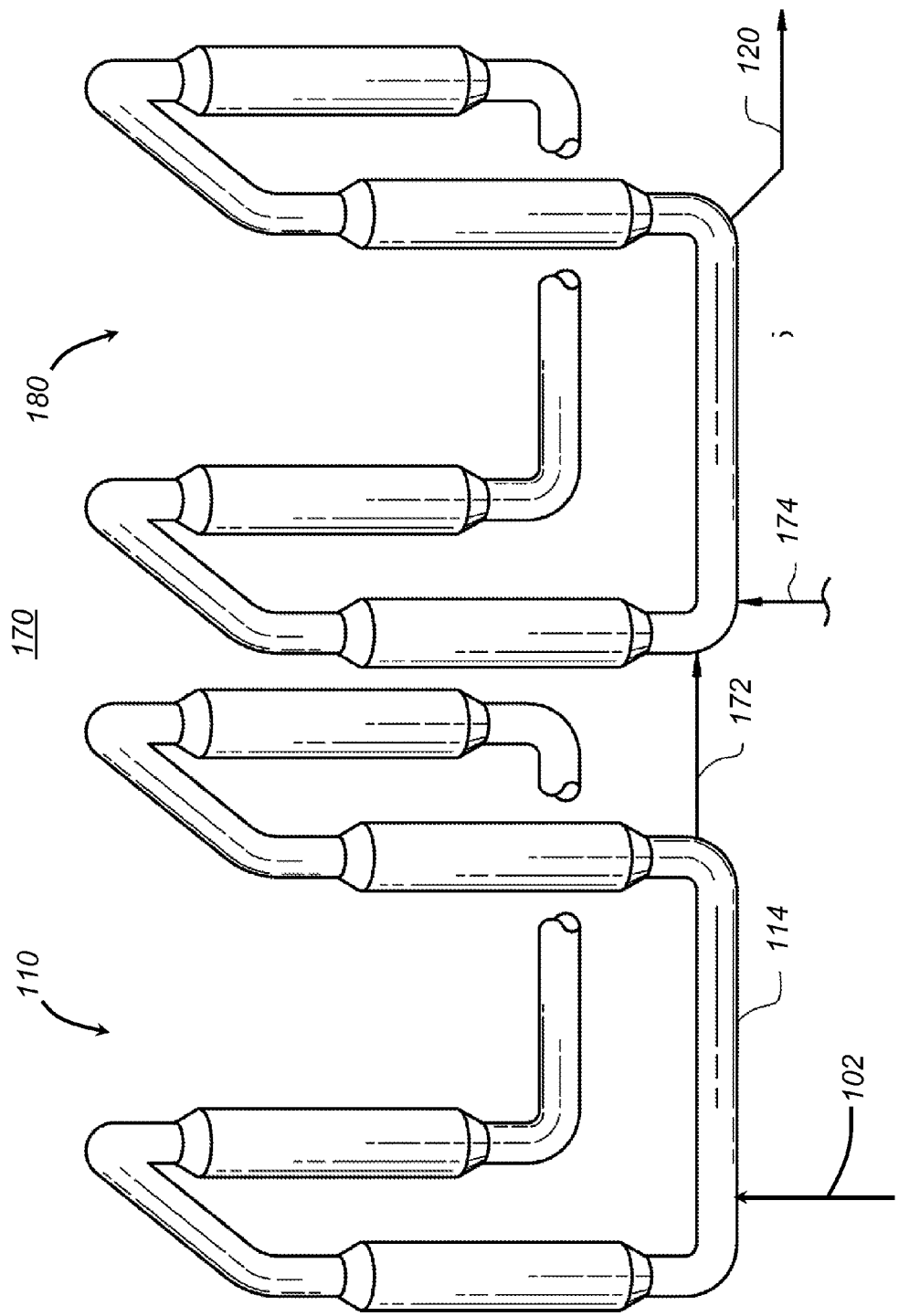
FIG. 2 schematically illustrates another process flow diagram of an embodiment of a loop polymerization process.

In embodiments having multiple reactors as shown in FIG. 2, production of polymerization product in multiple reactors 110, 180 may include several stages in at least two separate polymerization reactors 110, 180 interconnected by a transfer device or line 172 making it possible to transfer the polymerization product resulting from a first polymerization reactor 110 into a second reactor 180. The desired polymerization conditions in one reactor may be different from the polymerization conditions of the other reactor(s). Alternatively, polymerization in multiple reactors may include the manual transfer of polymerization product (e.g., in a polymerization product slurry, as a mixture, as solid polymer, or combinations thereof) from one reactor to subsequent reactors for continued polymerization. In addition to transferring some portion of the polymerization product to the second reactor 180, one or more components of the feed (e.g., diluent, catalyst, monomers, comonomers, etc.) may be feed through an inlet line as feed stream 174 into the second reactor 180. While illustrated in FIG. 2 as multiple loop reactors, multiple reactor systems may include any combination including, but not limited to, multiple loop reactors, a combination of loop and gas reactors, multiple high pressure reactors or a combination of high pressure reactors with loop and/or gas reactors. The multiple reactors may be operated in series, in parallel, or combinations thereof.

Returning to FIG. 1, the loop slurry polymerization reactor 110 may comprise vertical and/or horizontal pipes 112 and 114 (respectively) interconnected by smooth bends or elbows 115, which together form a loop. Portions of the loop slurry polymerization reactor 110, such as pipes 112, may have cooling jackets 113 placed therearound to remove excess heat generated by the exothermic polymerization reactions. A cooling fluid may be circulated through an annulus between the jackets 113 and the outer surface of the reactor 110, for example. The circulation of the cooling fluid may remove heat from the loop slurry polymerization reactor 110 through the reactor wall. The cooling fluid may be circulated to a cooling system to discharge the heat before returning to the annular region in a cooling cycle. The cooling jacket(s)s 113 may only cover a portion of the loop slurry polymerization reactor 110 and the intermediate regions may not be subject to heat transfer (e.g., heat removal). In an embodiment, at least about 10%, at least about 20%, at least about 30%, at least about 40%, at least about 50%, or at least about 60% of the outer surface of the loop slurry polymerization reactor 110 may be subject to heat exchange.

A motive device, such as pump 150, may circulate the fluid slurry in the loop slurry polymerization reactor 110. An example of the pump 150 is an in-line axial flow pump with a pump impeller 152 disposed within the interior of the reactor 110. The impeller 152 may, during operation, create a turbulent mixing zone within a fluid medium circulating through the reactor 110 such that sufficient contact between different polymerization components within the slurry may occur. The impeller 152 may also assist in propelling the slurry through the closed loop of the reactor 110 at sufficient speed to keep solid particulates, such as the catalyst or polymerization product, suspended within the slurry. The impeller 152 may be driven by a motor 154 or other motive force.

The system 100 may additionally comprise any equipment associated with a polymerization reactor, such as pumps, control devices (e.g., a PID controller), measurement instruments (e.g., thermocouples, transducers, and flow meters), alternative inlet and outlet lines, and the like.

Monomer, diluent, catalyst, and optionally any comonomer, which may be fed to the slurry loop polymerization reactor 110 (e.g., via feed stream 102), may circulate through the loop as polymerization occurs. Generally, continuous processes may comprise the continuous introduction of a monomer, an optional comonomer, a catalyst, and a diluent into the loop slurry polymerization reactor 110 and the continuous removal (e.g., via first line 120) of a slurry comprising solid polymer (e.g., polyethylene) and a liquid phase of the diluent.

In one or more embodiments, a comonomer may comprise unsaturated hydrocarbons having 3 to 20 carbon atoms. For example, a comonomer may comprise alpha olefins, such as for example propene, propylene, 1-butene, 1-pentene, 1-hexene, 3-methyl-1-butene, 4-methyl-1-pentene, 1-heptene, 1-octene, 1-nonene, 1-decene, and the like, or combinations thereof.

In embodiments, suitable diluents used in slurry polymerization processes may include, but are not limited to, the monomer, and optionally, the comonomer, being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. In embodiments, diluents may comprise unsaturated hydrocarbons having 3 to 12 carbon atoms. Further examples of suitable diluents include, but are not limited to, propene, 1-butene, 1-hexene, octenes, or combinations thereof. Some loop polymerization reactions can occur under bulk conditions where no diluent is used. An example is polymerization of propylene monomer as disclosed in U.S. Pat. No. 5,455,314, which is incorporated by reference herein in its entirety.

Additional information for typical loop polymerization processes is disclosed, for example, in U.S. Pat. Nos. 3,248,179, 4,501,885, 5,565,175, 5,575,979, 6,239,235, and 6,262,191, each of which is incorporated by reference in its entirety herein.

In embodiments having multiple reactors, various types of reactors that may additionally be included in system 100 may comprise gas-phase reactors. Gas-phase reactors may comprise fluidized bed reactors or staged horizontal reactors. Gas-phase reactors may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Likewise, copolymer product may optionally be withdrawn from the reactor and new or fresh comonomer may be added to replace polymerized comonomer, polymerized monomer, or combinations thereof. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone.

In embodiments having multiple reactors, various types of reactors that may additionally be included in system 100 may comprise loop slurry polymerization reactors. Such reactors may have a loop configuration, such as the configuration of the loop slurry polymerization reactor 110 of FIG. 1.

In embodiments having multiple reactors, various types of reactors that may additionally be included in system 100 may comprise high pressure reactors. High pressure reactors may comprise autoclave or tubular reactors. Tubular reactors may have several zones where fresh monomer (and optionally, comonomer), initiators, or catalysts may be added. Monomer (optionally, comonomer) may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

In embodiments having multiple reactors, various types of reactors that may additionally be included in system 100 may comprise a solution polymerization reactor wherein the monomer (optionally, comonomer) may be contacted with the catalyst composition by suitable stirring or other means. A carrier comprising an inert organic diluent or excess monomer (optionally, comonomer) may be employed. If desired, the monomer and/or optional comonomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means may be utilized for dissipating the exothermic heat of polymerization.

Conditions of a polymerization reactor, e.g., loop slurry polymerization reactor 110, which may be chosen and even controlled for polymerization efficiency and to provide resin properties include temperature, pressure and the concentrations of various reactants. Polymerization temperature can affect catalyst productivity, polymer molecular weight and molecular weight distribution. Suitable polymerization temperature may be any temperature below the de-polymerization temperature according to the Gibbs Free energy equation. Typically this includes the range from about 140° F. (about 60° C.) to about 536° F. (about 280° C.), for example, and from about 158° F. (about 70° C.) to about 230° F. (about 110° C.), depending upon the type of polymerization reactor.

Suitable pressures will also vary according to the reactor and polymerization type. The pressure for liquid phase polymerizations in a loop reactor such as loop slurry polymerization reactor 110 is typically less than about 1,000 psig, for example, about 650 psig. Pressure for gas phase polymerization is usually at about 200 psig to about 500 psig. High pressure polymerization in tubular or autoclave reactors is generally run at about 20,000 psig to about 75,000 psig. Polymerization reactors can also be operated in a supercritical region occurring at generally higher temperatures and pressures. Operation above the critical point of a pressure/temperature diagram (supercritical phase) may offer advantages. In an embodiment, polymerization may occur in an environment having a suitable combination of temperature and pressure. For example, polymerization may occur at a pressure in a range of about 400 psi to about 1,000 psi; alternatively, about 550 psi to about 650 psi, alternatively, about 600 psi to about 625 psi; and a temperature in a range of about 150° F. (about 66° C.) to about 230° F. (about 110° C.), alternatively, from about 195° F. (about 91° C.) to about 220=° F. (about 104° C.).

The concentration of various reactants can be controlled to produce solid polymer with certain physical and mechanical properties. The proposed end-use product that will be formed by the solid polymer and the method of forming that product determines the desired properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological measurements.

The concentrations and/or partial pressures of monomer, comonomer, hydrogen, co-catalyst, activator-support, modifiers, and electron donors are important in producing these resin properties. Comonomer may be used to control product density. Hydrogen may be used to control product molecular weight. Cocatalysts can be used to alkylate, scavenge poisons and control molecular weight. Activator-support can be used to activate and support the catalyst. Modifiers can be used to control product properties and electron donors affect stereoregularity, the molecular weight distribution, or molecular weight. In addition, the concentration of poisons is minimized because poisons impact the reactions and product properties.

Polymerization reaction components of the reactor(s) disclosed herein (e.g., loop slurry polymerization reactor 110) may include olefin monomers (e.g., ethylene) and comonomers (e.g., 1-hexene), diluent (e.g., isobutane, hexane, propane, or combinations thereof), molecular weight control agents (e.g., hydrogen), and any other desired co-reactants or additives. Polymerization reaction components may additionally include a catalyst, and optionally, a co-catalyst. Suitable catalyst for polymerizing the monomers and any comonomers may include, but is not limited to a catalyst(s) and, optionally, a co-catalyst(s) and/or a promoter(s). Nonlimiting examples of suitable catalyst systems include Ziegler Natta catalysts, Ziegler catalysts, chromium catalysts, chromium oxide catalysts, chromocene catalysts, metallocene catalysts, nickel catalysts, or combinations thereof. Nonlimiting examples of co-catalyst include triethylboron, methyl aluminoxane, alkyls such as triethylaluminum, or combinations thereof. Suitable activator-supports may comprise solid super acid compounds. Catalyst systems suitable for use in this disclosure have been described, for example, in U.S. Pat. Nos. 7,619,047; 7,790,820; 7,163,906; 7,960,487, each of which is incorporated by reference herein in its entirety.

The reaction components may be introduced to an interior of the loop slurry polymerization reactor 110 via inlets or conduits at specified locations, such as feed line 102. Any combination of the reaction components identified above (and others known to those skilled in the art), together with any catalyst and/or co-catalyst described herein, may form a suspension, i.e., a slurry, that circulates through the loop formed by the loop slurry polymerization reactor 110.

The slurry may circulate through the loop slurry polymerization reactor 110, and monomers (and optionally, comonomers) may polymerize to form a polymerization product. The polymerization product may comprise a polymerization product slurry, a product mixture, or combinations thereof.

In embodiments, the polymerization product slurry may comprise solid polymer and a liquid phase of a diluent. In an embodiment, the polymerization product slurry may comprise unreacted monomer and/or unreacted comonomer in a liquid phase. In additional or alternative embodiments, the polymerization product slurry may generally comprise various solids, semi-solids, volatile and nonvolatile liquids, or combinations thereof. In an embodiment, the polymerization product slurry may comprise one or more of hydrogen, nitrogen, methane, ethylene, ethane, propylene, propane, butane, isobutane, pentane, hexane, 1-hexene and heavier hydrocarbons. In an embodiment, ethylene may be present in a range of from about 0.1% to about 15%, alternatively, from about 1.5% to about 5%, alternatively, about 2% to about 4% by total weight of the liquid in the product line. Ethane may be present in a range of from about 0.001% to about 4%, alternatively, from about 0.2% to about 0.5% by total weight of the material in the product line. Isobutane may be present in a range from about 80% to about 98%, alternatively, from about 92% to about 96%, alternatively, about 95% by total weight of the material in the product line.

In embodiments, the product mixture may comprise the solid polymer and a vapor phase of at least a portion of the diluent. In additional or alternative embodiments, the mixture may comprise unreacted, gaseous monomers or optional comonomers (e.g., unreacted ethylene monomers, unreacted 1-butene monomers), gaseous waste products, gaseous contaminants, or combinations thereof. As used herein, an "unreacted monomer," for example, ethylene, refers to a monomer that was introduced into a polymerization reactor during a polymerization reaction but was not incorporated into a polymer. As used herein, an "unreacted comonomer," for example, 1-butene, refers to a comonomer that was introduced into a polymerization reactor during a polymerization reaction but was not incorporated into a polymer. Such gaseous phase product mixtures may be present when gas phase reactors are used in place of or in addition to a loop slurry reactor.

In embodiments, the solid polymer product may comprise a homopolymer, a copolymer, or combinations thereof. The homopolymer and/or the polymers of the copolymer may comprise a multimodal (e.g., a bimodal) polymer (e.g., polyethylene). For example, the solid polymer may comprise both a relatively high molecular weight, low density (HMWLD) polyethylene polymer component and a relatively low molecular weight, high density (LMWHD) polyethylene polymer component. Various types of suitable polymers may be characterized as having a various densities. For example, a Type I may be characterized as having a density in a range of from about 0.910 g/cm$^3$ to about 0.925 g/cm$^3$, alternatively, a Type II may be characterized as having a density from about 0.926 g/cm$^3$ to about 0.940 g/cm$^3$, alternatively, a Type III may be characterized as having a density from about 0.941 g/cm$^3$ to about 0.959 g/cm$^3$, alternatively, a Type IV may be characterized as having a density of greater than about 0.960 g/cm$^3$. The solid polymer may comprise other polyolefin polymers.

The polymerization product (e.g., polymerization product slurry) may be withdrawn from one or more reactors present in system 100, e.g., the loop slurry polymerization reactor 110, via first line 120. The withdrawn polymerization product may be conveyed through the first line 120 to a separation vessel 140. The line 120 may be referred to as a flashline between reactor 110 and separation vessel 140, wherein a portion, substantially all, or all (e.g., 100%) of liquid phase components present in the polymerization product are converted to gas phase components. The polymerization product may be conveyed to the separation vessel 140. The flash line may comprise a variable inner diameter, which may increase in the direction of flow. In embodiments, the upstream portion of the flash line may have an inner diameter of about 1 inch to about 8 inches, and the downstream portion may have an inner diameter of about 2 inches to about 10 inches.

In an embodiment, a polymerization product slurry in the polymerization product may convert to an at least partial gas phase product mixture in the line 120. Thus, in embodiments, the polymerization product conveyed through line 120 may be in the form of a liquid polymerization product slurry (e.g., a slurry of solid polymer and liquid phase diluent and/or unreacted monomer/comonomer), a gas phase product mixture (e.g., solid polymer and gas phase diluent and/or unreacted monomer/comonomer), or combinations thereof (e.g., a three-phase mixture of liquid and gaseous diluent and/or unreacted monomer/comonomer and solid polymer), and the form of the polymerization product may be a function of the conditions (e.g., temperature and pressure) present at a given location in line 120.

In an embodiment, polymer product withdrawn from the loop slurry polymerization reactor 110 may be conveyed through the line 120 via the total pressure differential between the operating pressure of the loop slurry polymerization reactor 110 and the separation vessel 140. In an embodiment, the polymerization product (e.g., polymerization product slurry, mixture, or combinations thereof) may be conveyed through the line 120, which may comprise a continuous take-off valve, to yield an at least partial gas phase mixture (e.g., mixture of gas phase diluent and/or unreacted monomer/comonomer and solid polymer). In an embodiment, a valve may be present in the line 120. The position of the separation vessel 140 relative to the loop slurry polymerization reactor 110 may be adjusted in order to transfer withdrawn polymer product via the total pressure differential, for example, to minimize or reduce the equipment dedicated to polymer product conveyance, to volatilize all liquid in the polymer product, or combinations thereof. In an embodiment, the total pressure differential may be the sole means for conveying polymer product between the loop slurry polymerization reactor 110 and separation vessel 140.

The separation vessel 140 may recover solid polymer which is received from the line 120. In one or more of the embodiments disclosed herein, the polymerization product flowing from the line 120 (for example, a mixture of solid polymer and at least a portion, substantially all or all of the other components, e.g., diluent and/or unreacted monomer/ comonomer, are in a gas phase) may be separated in separation vessel 140 into solid polymer in line 144 and one or more gases in line 142.

Any suitable technique may be used to separate the polymerization product into solid polymer and gases. For example, the separation vessel 140 may comprise a vapor-liquid separator. Suitable embodiments of a vapor-liquid separator may include a distillation column, a flash tank, a filter, a membrane, a reactor, an absorbent, an adsorbent, a molecular sieve, a cyclone, or combinations thereof. In an embodiment, the separator comprises a flash tank. Not seeking to be bound by theory, such a flash tank may comprise a vessel configured to vaporize and/or remove low vapor pressure components from a high temperature and/or high pressure fluid.

In an embodiment, the separation vessel 140 may be configured such that polymerization product from the line 120 may be separated into solid and liquid (e.g., a condensate) phase components in line 144 and a gas (e.g., vapor) phase components in line 142. The liquid or condensate may comprise solid polymer (e.g., polyethylene) and any liquid phase components such as diluent and/or unreacted monomer/comonomer, and in some embodiments line 144 is a concentrated slurry in comparison to the product slurry in line 120. The gas or vapor may comprise volatile solvents, diluent, unreacted monomers and/or optional comonomers, waste gases (e.g., secondary reaction products, such as contaminants and the like), or combinations thereof. The separations vessel 140 may be configured such that the polymerization product flowing from the line 120 is flashed by heat, pressure reduction, or combinations thereof such that the enthalpy of the line is increased. This may be accomplished via a heater, a flashline heater, various other operations commonly known in the art, or combinations thereof. For example, a flash line heater comprising a double pipe may exchange heat by hot water or steam. Such a flashline heater may increase the temperature of the line 120 while reducing its pressure.

In an alternative embodiment, the separation vessel 140 may be configured such that polymerization product from line 120 may be separated into solid polymer in line 144 substantially or completely free of any liquid phase components and one or more gases in line 142. Suitable separation techniques include distilling, vaporizing, flashing, filtering, membrane screening, absorbing, adsorbing, cycloning, gravity settling, or combinations thereof, the polymerization product received in separation vessel 140 from the line 120.

In an embodiment, the separation vessel 140 may operate at a pressure of from about 50 psig to about 500 psig; alternatively, from about 130 psig to about 190 psig; and further alternatively, at an operating pressure of about 135 psig.

In one or more embodiments, the gas in line 142 may comprise hydrogen, nitrogen, methane, ethylene, ethane, propylene, propane, butane, isobutane, pentane, hexane, 1-hexene and heavier hydrocarbons. In an embodiment, ethylene may be present in a range of from about 0.1% to about 15%, alternatively from about 1.5% to about 5%, alternatively, about 2% to about 4% by total weight of the line. Ethane may be present in a range of from about 0.001% to about 4%, alternatively from about 0.2% to about 0.5% by total weight of the line. Isobutane may be present in a range from about 80% to about 98%, alternatively from about 92% to about 96%, alternatively, about 95% by total weight of the line.

The separation vessel 140 may additionally comprise any equipment associated with the separation vessel 140, such as control devices (e.g., a PID controller) and measurement instruments (e.g., thermocouples), and level control and measurement devices.

In an embodiment, the slurry may be removed from loop slurry polymerization reactor 110 by the use of one or more settling legs. The settling leg may be an alternative removal device or in addition to the line 120. In this embodiment, a portion of the product slurry can be continuously or periodically drawn off from the reactor loop into a relatively short segment of piping in a generally vertically positioned relative to the loop horizontal line. The product slurry draw may be controlled in rate or amount by a receiver valve and into a sloped or slanted (canted) leg. Once the product slurry, and particularly the solid polymer product, is received in the settling leg, the reactor effluent can be flashed to remove the solid polymer from the liquids (e.g., the diluent, monomer, comonomer, etc.). Various technologies can be used for this separation step including but not limited to, flashing that can include any combination of heat addition and pressure reduction, separation by cyclonic action in either a cyclone or hydrocyclone, or separation by centrifugation. The solid polymer product having a portion, substantially all, or all of the liquid removed can then be passed to one or more downstream processing units.

In general, the polymerization process is exothermic, thereby generating heat at the polymerization site and increasing the temperature of the slurry within the loop slurry polymerization reactor 110. In order to control the polymerization reaction and the slurry polymer product, the heat can be controlled by removing the heat through the loop slurry polymerization reactor 110 walls. For example, the heat may pass from the slurry to the loop slurry polymerization reactor 110 walls, through the loop slurry polymerization reactor 110 walls, and into a cooling fluid in contact with an exterior surface of the loop slurry polymerization reactor 110, thereby generating (or resulting in) a heat transfer pathway.

Figure 3A:
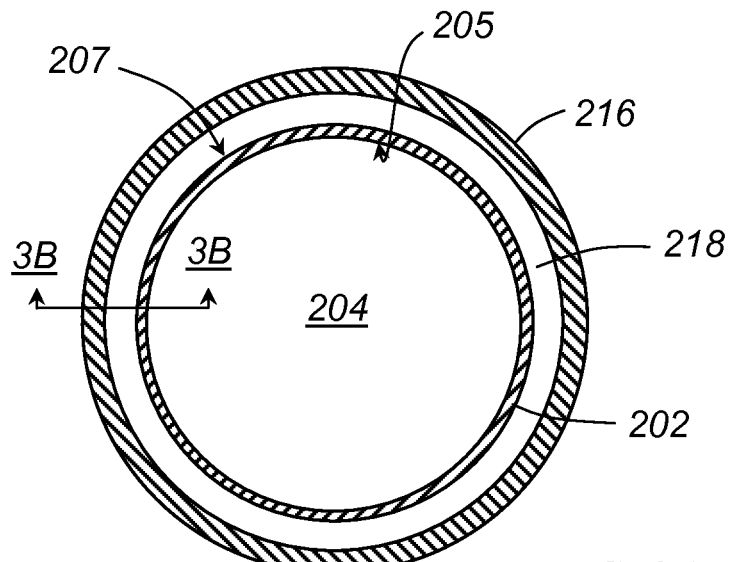
FIGS. 3A-3B illustrate cross-sectional views of a portion of a loop polymerization reactor.
Figure 3B:
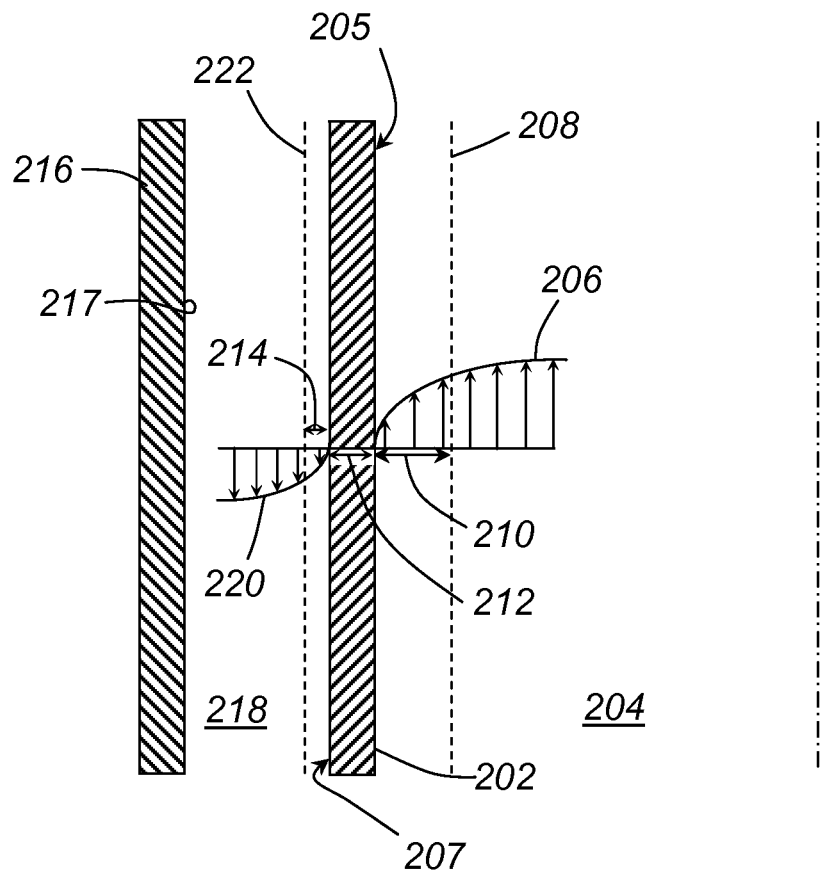

As schematically illustrated in FIGS. 3A and 3B, multiple resistances to heat transfer may be present within the heat transfer pathway from the polymer product slurry 204 to the coolant 218. In an embodiment, the slurry 204 in the loop slurry polymerization reactor 110 may form a slurry film having a film coefficient along an inner surface 205 of the wall 202 of the loop slurry polymerization reactor 110. The slurry film may present a resistance to heat transfer from the bulk slurry 204 (e.g., the reaction mixture) to the reactor wall 202. Further, the loop slurry polymerization reactor 110 comprises a wall 202 having a thickness 212 and a thermal conductivity, and the reactor wall 202 itself may also present a resistance to heat transfer. After passing through the wall 202 of the loop slurry polymerization reactor 110, the heat may then be transferred to the coolant 218, which may have a film effect between the outer surface of the reactor wall 202 and the coolant fluid 218 (e.g., as shown by coolant film boundary 222). In order to effectively remove heat from the loop slurry polymerization reactor 110, the resistance to heat transfer in each portion of the heat transfer path can be analyzed. The design of the loop slurry polymerization reactor 110, the operating conditions/parameters within the loop slurry polymerization reactor 110, the coolant operating parameters, and the like can be selected or controlled to effectively transfer heat from the polymer slurry. This may represent the operation of the polymerization system under one or more conditions such that the contribution of the resistance to heat transfer through the slurry film is balanced with respect to the resistances to heat transfer through the reactor wall 202 and/or the coolant film. In an embodiment, the system may be operated under one or more conditions such that the contribution of the resistance to heat transfer through the slurry film is less than a resistance to heat transfer through the reactor wall 202 and/or the coolant film or fluid, thereby improving the heat transfer from the polymerization reaction.

The heat transfer pathways within the polymerization system are schematically illustrated in FIG. 3B. The slurry 204 is present within the loop slurry polymerization reactor 110 and contacts the interior surface of the reactor wall 202. When the slurry 204 flows through the loop slurry polymerization reactor 110 during use, a velocity profile 206 is established. In general, the velocity may be substantially zero, or at least substantially reduced, at the reactor wall 202. The velocity profile 206 demonstrates that the slurry velocity may increase to a bulk slurry velocity within the loop slurry polymerization reactor 110, which may comprise a turbulent flow as the velocity profile moves away from the reactor wall 202. A slurry film layer denoted by the slurry film boundary 208 may be formed near the inner surface 205 of the reactor wall 202. In the slurry film, the velocity of the slurry 204 may be less than the velocity of the bulk slurry flow. The slurry film boundary 208 may generally be taken as the point or surface at which the slurry velocity is at least about 95%, at least about 96%, at least about 97%, at least about 98%, or at least about 99% of the freestream velocity. The slurry film thickness may then be taken as the distance 210 between the interior surface 205 of the reactor wall 202 and the slurry film boundary 208.

Heat transfer through the slurry film layer may be characterized by a slurry film coefficient. The slurry film coefficient characterizes the amount of heat transferred per area, time, and the existing temperature differential (e.g., the temperature gradient) between the bulk slurry and the reactor wall 202 through the slurry film layer. The slurry film coefficient may be determined using any known techniques. An approximation of the slurry film coefficient is provided by Eq. 1.

$$h_{slurry} = \frac{f}{2} \cdot \frac{K_s}{D_i} \cdot (Pr_s)^{\frac{1}{3}} \cdot Re_s \qquad \text{(Eq. 1)}$$

In Eq. 1, $h_{slurry}$ is the slurry film coefficient in units of Btu/(hr)(ft$^2$)(° F.) (e.g., which can also be expressed as BTU·hr$^{-1}$·ft$^{-2}$·° F.$^{-1}$), f is the Fanning friction factor, $K_s$ is the thermal conductivity of the reactor slurry in units of Btu/(hr)(ft)(F), $D_i$ is the inner diameter of the reactor wall in units of (ft), $Pr_s$ is the Prandtl number of the slurry, and $Re_s$ is the Reynolds number of the slurry, where the Fanning friction factor, the Prandtl number, and the Reynolds number are dimensionless. One of ordinary skill in the art, with the aid of this disclosure, may determine the Fanning friction factor, the Prandtl number, and the Reynolds number for a given geometry. For example, the Fanning Friction factor (f) for laminar flow in a cylindrical tube is represented by the equation:

$$f = 16/Re_s \qquad \text{(Eq. 2)}$$

The Reynolds number of the slurry (Res) is the ratio of the inertial forces to the viscous forces in the slurry. In an embodiment, the Reynolds number of the slurry can be represented by the equation:

$$Re_s = \frac{D_i \cdot V_s \cdot \rho_s}{\mu_s} \qquad \text{(Eq. 3)}$$

where $V_s$ is the velocity of the slurry in (ft)(s$^{-1}$), $\rho_s$ is the slurry density in (lb)(ft$^{-3}$) and $\mu_s$ is the slurry viscosity in (lb)(ft$^{-1}$)(s$^{-1}$). The Prandtl number of the slurry (Prs) is the ratio of the kinematic viscosity to the thermal diffusivity rate. In an embodiment, the Prandtl number of the slurry can be represented by the equation $$Pr_s = \frac{Cp_s \cdot \mu_s \cdot 3600}{\kappa_s} \qquad \text{(Eq. 4)}$$

where $Cp_s$ is the specific heat capacity of the slurry in (Btu)(lb$^{-1}$)(° F.$^{-1}$), $\rho_s$ is the slurry density in (lb)(ft$^{-3}$), $\kappa_s$ is the thermal conductivity of the slurry in units of (Btu)(hr$^{-1}$)(ft$^{-1}$)(° F.$^{-1}$), and the factor of 3600 is for the conversion of hours to seconds.

The slurry film coefficient, $h_{slurry}$, may be affected by any of the variables presented in Eqs. 1-4, which are in turn affected by various slurry parameters and operating conditions within the loop slurry polymerization reactor 110. In an embodiment, the slurry film coefficient may be greater than about 200 BTU·hr$^{-1}$·ft$^{-2}$·° F.$^{-1}$, greater than about 250 BTU·hr$^{-1}$·ft$^{-2}$·° F.$^{-1}$, greater than about 300 BTU·hr$^{-1}$·ft$^{-2}$·° F.$^{-1}$, greater than about 350 BTU·hr$^{-1}$·ft$^{-2}$·° F.$^{-1}$, greater than about 400 BTU·hr$^{-1}$·ft$^{-2}$·° F.$^{-1}$, or greater than about 450 BTU·hr$^{-1}$·ft$^{-2}$·° F.$^{-1}$. In an embodiment, the slurry film coefficient may be less than about 500 BTU·hr$^{-1}$·ft$^{-2}$·° F.$^{-1}$, less than about 450 BTU·hr$^{-1}$·ft$^{-2}$·° F.$^{-1}$, or less than about 400 BTU·hr$^{-1}$·ft$^{-2}$·° F.$^{-1}$. In some embodiments, other ranges of the slurry film coefficient are possible based on the reaction conditions and the slurry composition. For example, the slurry film coefficient may be greater than about 600 BTU·hr$^{-1}$·ft$^{-2}$·° F.$^{-1}$, greater than about 700 BTU·hr$^{-1}$·ft$^{-2}$·° F.$^{-1}$, greater than about 800 BTU·hr$^{-1}$·ft$^{-2}$·° F.$^{-1}$, greater than about 900 BTU·hr$^{-1}$·ft$^{-2}$·° F.$^{-1}$, greater than about 1,000 BTU·hr$^{-1}$·ft$^{-2}$·° F.$^{-1}$, greater than about 1,100 BTU·hr$^{-1}$·ft$^{-2}$·° F.$^{-1}$, greater than about 1,200 BTU·hr$^{-1}$·ft$^{-2}$·° F.$^{-1}$, or greater than about 1,300 BTU·hr$^{-1}$·ft$^{-2}$·° F.$^{-1}$. In an embodiment, the slurry film coefficient may be less than about 1,400 BTU·hr$^{-1}$·ft$^{-2}$·° F.$^{-1}$ or less than about 1,350 BTU·hr$^{-1}$·ft$^{-2}$·° F.$^{-1}$.

Various factors may affect the slurry film coefficient, $h_{slurry}$. In an embodiment, the solids content of the slurry, the slurry velocity, the relative roughness of the interior surface of the reactor, the reactor diameter, and any other flow properties of the slurry may affect the calculation of the slurry film coefficient. In general, an increase in the solids content of the slurry may result in a reduction in the slurry film coefficient. The resistance to heat transfer through the slurry film is represented by the inverse of the slurry film coefficient (e.g., 1/$h_{slurry}$), and a reduction in the slurry film coefficient represents an increase in the resistance to heat transfer through the slurry film. In an embodiment, the solids content of the slurry may be greater than about 25%, greater than about 30%, greater than about 35%, greater than about 40%, greater than about 45%, greater than about 50%, greater than about 55%, or greater than about 60% by weight. In some embodiments, the solids content of the slurry may be less than about 80%, less than about 75%, less than about 70%, less than about 65%, or less than about 60% by weight. In an embodiment, the volume fraction of the solids in the slurry may be greater than about 0.15, greater than about 0.2, greater than about 0.25, greater than about 0.3, greater than about 0.35, greater than about 0.4, greater than about 0.45, greater than about 0.5, greater than about 0.55, greater than about 0.6, greater than about 0.65, or greater than about 0.7. In an embodiment, the volume fraction of the solids in the slurry may be less than about 0.9, less than about 0.85, less than about 0.8, less than about 0.75, less than about 0.7, or less than about 0.65. In an embodiment, the volume fraction of the solids in the slurry is greater than or equal to about 0.65. One of ordinary skill in the art with the aid of this disclosure can recognize that the solids content of the slurry can be converted between a weight basis and a volume basis using various factors such as the solids density and/or the conditions within the reactor 110.

The slurry velocity may affect the Reynolds number and thereby the slurry film coefficient. As described above, the slurry may circulate in the loop slurry polymerization reactor 110, for example, in response to the action of the pump 150 or impeller 152. In general, an increase in the slurry velocity is expected to result in an increase in the slurry film coefficient, $h_{slurry}$, thereby decreasing the resistance to heat transfer through the slurry film. In an embodiment, the slurry velocity within the reactor may be greater than about 20 ft/s, 25 ft/s, about 30 ft/s, about 35 ft/s, about 40 ft/s, or about 45 ft/s. In some embodiments, the slurry velocity within the reactor may be less than about 55 ft/s or less than about 50 ft/s. In an embodiment, the slurry velocity is greater than about 30 ft/s.

The relative roughness of the interior surface 205 of the reactor may also affect the slurry film coefficient. The roughness of the surface may affect the slurry film coefficient, but may also affect the degree to which the interior surface of the reactor is subject to fouling. In general, as the roughness of the interior reactor wall increases so does the risk of fouling. An increase in the roughness of the interior wall may increase the Reynolds number and thereby increase the slurry film coefficient, $h_{slurry}$. While the roughness may contribute to a reduced resistance to heat transfer through the slurry film, this benefit may be outweighed if fouling occurs so that a layer of polymer accumulates on the internal surface 205. The accumulated layer of polymer may have a relatively low thermal conductivity compared to the reactor wall 202, and may act as an insulating layer within the loop slurry polymerization reactor 110. In terms of reducing the resistances to heat transfer along the heat transfer pathway, it may then be counterintuitive to reduce the internal surface roughness to improve heat transfer to the reactor wall 202 through the slurry film layer.

The surface roughness can be determined using a variety of tests such as the arithmetic mean roughness value specified by the methods of standard tests DIN 4768/1, DIN 4762/1, or ISO/DIS 4287/1. Alternatively, the root mean square (RMS) roughness value may be specified by the methods of standard tests DIN 4762/1 or ISO 4287:1997. The RMS value is generally determined over a surface profile calculated over a sampling length, or alternatively over the mean result of multiple sampling lengths (e.g., 5 sampling lengths). The RMS value is generally expressed in terms of RMS microinches. The RMS value can be converted into various units of length according to the standard, and the base RMS value is expressed in units of microinches (e.g., 100 RMS is 100 root-mean-square microinches). In general, various processes can be used to polish a surface and reduce the roughness value. For example, mechanical polishing can be used to reduce the surface roughness to between about 60 RMS to 70 RMS (e.g., 60 to 70 root-mean-square microinches). Further treatments such as chemical polishing or electromechanical processes can further reduce the surface roughness value over the mechanically polished value. Using such various procedures can result in a final surface roughness of less than about 20 RMS (e.g., 20 root-mean-square microinches). In an embodiment, the interior surface of the reactor can be treated to obtain a final surface roughness value of less than about 100 RMS microinches, less than about 60 RMS microinches, less than about 50 RMS microinches, less than about 40 RMS microinches, less than about 30 RMS microinches, less than about 20 RMS microinches, or less than about 15 RMS microinches. In an embodiment, the surface roughness value of the interior surface of the reactor may be between about 10 RMS microinches and about 30 RMS microinches.

Within the heat transfer pathway as illustrated in FIG. 3B, the heat may pass through the reactor wall 202 once it has passed from the bulk slurry 204 to the reactor wall 202 through the slurry film layer. The reactor wall 202 may present a resistance to heat transfer as the heat passes from the slurry 204 to the coolant 218. The reactor wall 202 comprises a thickness 212 and a thermal conductivity ($\mu$), where the thermal conductivity of the reactor wall 202 may affect the relative resistance to heat transfer through the reactor wall 202. The resistance to heat transfer through the reactor wall 202 may be characterized by the length of the conduction pathway divided by the thermal conductivity of the reactor wall 212. In general, an increased thermal conductivity may improve the heat transfer capability, and thereby reduce the resistance to heat transfer through the reactor wall 202. An increased heat transfer pathway length may reduce the heat transfer capability, and thereby present a greater resistance to heat transfer through the reactor wall 202. In an embodiment, the length of the conduction pathway in the reactor may be characterized by the thickness 212 of the reactor wall 202.

The thermal conductivity of the reactor wall 202 is based, at least in part, on the material used to form the loop slurry polymerization reactor 110. The reactor wall 202 may be formed of a suitable high-strength material sufficient to retain the slurry within the reactor at the reaction conditions (e.g., reaction temperature, pressure, flowrate, etc.). The reactor wall 202 can be constructed from a seamless pipe or pipe section, a rolled plate having the edges joined together, or the like. The formation method for the reactor wall 202 may affect the composition and design of the reactor. In an embodiment, the reactor wall 202 may be constructed using a steel having a suitable thermal conductivity and tensile strength (TS). The steel may comprise iron and carbon as well as other elements or additives including, but not limited to, aluminum, carbon, manganese, silicon, chromium, nickel, cobalt, molybdenum, copper, sulfur, phosphorus, tantalum, niobium, titanium, vanadium, and any combination thereof. It has been found that carbon, manganese, silicon, chromium, and/or nickel generally reduces the thermal conductivity of a steel while cobalt, molybdenum, copper, sulfur, phosphorus, and tantalum tend to increase the thermal conductivity. However, these elements also affect the minimum tensile strength (TS), weldability, and cost of the steel. Various grades of steel useful for forming the reactor, which may comprise one or more of the additives listed above, can include, but are not limited to, A106 Gr 8 (60), A516 Gr 70, A537 Cl 2, A106 Gr C (40), A202 Gr 8, A285 Gr C, A514 Gr 8, A515 Gr 70, A/SA516 grade 70, A517 Gr A, A517 Gr 8, A533 Ty A C13, A542 Ty A C12, A678 Gr C, AISI 1010, AISI 1015, MIL-S 24645, and any combination thereof. In an embodiment, the steel may comprise iron and one or more of the following elements: carbon in an amount of from about 0.05 wt % to about 0.25 wt %, silicon in an amount of from about 0.5 wt % to about 0.75 wt %, manganese in an amount of from about 0.8 wt % to about 2.0 wt %, phosphorous in an amount of from about 0.01 wt % to about 0.1 wt %, sulfur in an amount of from about 0.01 wt % to about 0.1 wt %, aluminum in an amount of from about 0.01 wt % to about 0.04 wt %, chromium in an amount of from about 0.1 wt % to about 0.5 wt %, copper in an amount of from about 0.1 wt % to about 0.5 wt %, nickel in an amount of from about 0.1 wt % to about 0.5 wt %, molybdenum in an amount of from about 0.05 wt % to about 0.1 wt %, niobium in an amount of from about 0.005 wt % to about 0.02 wt %, titanium in an amount of from about 0.01 wt % to about 0.05 wt %, and/or vanadium in an amount of from about 0.01 wt % to about 0.04 wt %. When the reactor wall is formed from steel, the steel may generally have a thermal conductivity of at least about 20 BTU/(hr) (ft)(° F.) (e.g., which may be represented as BTU·hr$^{-1}$·ft$^{-1}$·° F.$^{-1}$). In an embodiment, the steel may have a thermal conductivity (x) ranging from about 20 BTU·hr$^{-1}$·ft$^{-1}$·° F.$^{-1}$ to about 38 BTU·hr$^{-1}$·ft$^{-1}$·° F.$^{-1}$. The tensile strength of the steel may be determined using any suitable method, including for example, the version of ASTM EI/E8M in use at the time of filing the present description. The tensile strength may depend on the type of steel and its components, and may include tensile strength in the range of from about 600 MPa to about 1,100 MPa.

With regard to the dimensions of the reactor, the loop slurry polymerization reactor 110 may generally have an outer diameter between about 8 inches and 42 inches, or between about 10 inches and about 36 inches. The thickness 212 of the reactor wall 202 may vary based on the outer diameter of the loop slurry polymerization reactor 110 and the expected operating pressure, temperature, and the strength of the material forming the reactor. The thickness 212 of the reactor wall 202 may be suitable for retaining the slurry within the loop slurry polymerization reactor 110 over the range of expected operating conditions within the reactor. In an embodiment, the thickness of the reactor wall 202 may be greater than about 0.05 inches, greater than about 0.1 inches, greater than about 0.2 inches, greater than about 0.3 inches, greater than about 0.4 inches, greater than about 0.5 inches, greater than about 0.6 inches, greater than about 0.7 inches, greater than about 0.8 inches, greater than about 0.9 inches, or greater than about 1 inch. In an embodiment, the thickness of the reactor wall 202 may be less than about 2.5 inches, less than about 2.0 inches, less than about 1.9 inches, less than about 1.8 inches, less than about 1.7 inches, less than about 1.6 inches, less than about 1.5 inches, less than about 1.4 inches, less than about 1.3 inches, less than about 1.2 inches, less than about 1.1 inches, or less than about 1 inch.

The relative resistances to heat transfer from the slurry and into and through the reactor wall can be characterized using the Biot number. As used herein, the Biot number is defined as a dimensionless parameter indicative of the balance between the resistance to heat transfer through the reactor wall and the resistance to heat transfer through a fluid in contact with the reactor wall 202. The Biot number may also be understood in terms of the heat transfer mechanisms present along the heat transfer pathway. For example, the Biot number can be understood as representing the relative resistance to conductive heat transfer through the reactor wall 202 relative to the convective heat transfer from the slurry 204 or the coolant 218 to the reactor wall 202. The value of the Biot number provides an indication of the location and magnitude of the resistance to heat transfer. The results of the determination of the Biot number may then be used to design the reactor wall, determine operating conditions within the reactor and/or coolant, and the like.

An internal Biot number may be defined as a dimensionless parameter indicative of the balance between the resistance to heat transfer through the reactor wall and the resistance to heat transfer through the slurry film layer in contact with the reactor wall 202. The internal Biot number may be defined using the following equation:

$$B_{int} = \frac{h_{SLURRY} \cdot L_R}{k_R} \quad \text{(Eq. 5)}$$

where $B_{int}$ is the internal Biot number, $h_{slurry}$ is the slurry film coefficient defined above in units of BTU·hr$^{-1}$·ft$^{-2}$·° F.$^{-1}$, $L_R$ is the characteristic length of the reactor wall (e.g., the thickness 212) in units of ft$^{-1}$, and $k_R$ is the thermal conductivity of the reactor wall in units of BTU·hr$^{-1}$·ft$^{-1}$·° F.$^{-1}$. The internal Biot number is referred to as "internal" since it represents the relative balance between the resistance to heat transfer through the reactor wall relative to the resistance to heat transfer through the slurry film within the reactor.

In general, a large value of the internal Biot number indicates that the conductive resistance to heat transfer through the reactor wall 202 controls the heat transfer from the loop slurry polymerization reactor 110. Conversely, a small value of the internal Biot number indicates that the convective resistance to heat transfer through the slurry to the interior surface of the reactor wall 202 controls the heat transfer from the loop slurry polymerization reactor 110. In an embodiment, the internal Biot number may be maintained at or below about 3.0, at or below about 2.0, at or below about 1.5, at or below about 1.1, or at or below about 1.0 within the reactor during the polymerization process.

Several other ratios may also be useful for operating the polymerization under one or more conditions such that the contribution of the resistance to heat transfer through the slurry film is balanced with respect to the resistances to heat transfer through the reactor wall 202 and/or the coolant film. In an embodiment, a ratio of the slurry film coefficient to the thermal conductivity of the reactor wall may be in a range of from about 8.0 ft$^{-1}$ to about 50 ft$^{-1}$, or in some embodiments from about 14 ft$^{-1}$ to about 35 ft$^{-1}$. In an embodiment, a ratio of the film coefficient to the thickness of the reactor wall may be in a range of from about 1,400 BTU·hr$^{-1}$·ft$^{-3}$·° F.$^{-1}$ to about 240,000 BTU·hr$^{-1}$·ft$^{-3}$·° F.$^{-1}$, or in some embodiments, in a range of from about 2,400 BTU·hr$^{-1}$·ft$^{-3}$·° F.$^{-1}$ to about 100,000 BTU·hr$^{-1}$·ft$^{-3}$·° F.$^{-1}$. In an embodiment, a ratio of the thermal conductivity to the thickness may be in a range of from about 100 BTU·hr$^{-1}$·ft$^{-2}$·° F.$^{-1}$ to about 10,000 BTU·hr$^{-1}$·ft$^{-2}$·° F.$^{-1}$, or in some embodiments, in a range of from about 120 BTU·hr$^{-1}$·ft$^{-2}$·° F.$^{-1}$ to about 4,000 BTU·hr$^{-1}$·ft$^{-2}$·° F.$^{-1}$. In some embodiments, the ratio of the thermal conductivity to the thickness may be greater than about 120 BTU·hr$^{-1}$·ft$^{-2}$·° F.$^{-1}$, greater than about 160 BTU·hr$^{-1}$·ft$^{-2}$·° F.$^{-1}$, greater than about 250 BTU·hr$^{-1}$·ft$^{-2}$·° F.$^{-1}$, or greater than about 300 BTU·hr$^{-1}$·ft$^{-2}$·° F.$^{-1}$.

As shown in FIG. 3A, the heat transfer pathway also comprises a coolant fluid 218 passing through the annulus formed between an outer jacket 216 and the outer surface 207 of the reactor wall 202. The coolant 218 may flow co-current, counter-current, or cross-current relative to the slurry flow 204 through the interior of the loop slurry polymerization reactor 110. Coolant 218 introduced into the annulus may flow around and in contact with the exterior surface of the reactor wall 202. Heat flowing through the reactor wall 202 may be exchanged between the reactor wall 202 and the coolant fluid 218, thereby allowing for the removal of heat from the interior of the reactor wall 202. After contacting the reactor wall 202, the coolant 218 may pass out of the annulus and pass to a separate heat exchanger unit where the transferred heat may be rejected to an exterior source.

Referring back to FIG. 3B, as with the slurry, a coolant velocity profile 220 may be established along the exterior surface of the reactor wall 202 when the coolant 218 flows through the annulus 217. In general, the velocity of the coolant 218 may be substantially zero or at least substantially reduced at the exterior surface of the reactor wall 202. The velocity profile 220 demonstrates that the coolant velocity may increase to a bulk coolant flow velocity within the annulus 217, and the coolant may have a turbulent flow within the annulus 217. A coolant film layer denoted by the coolant film boundary 222 may be formed near the outer surface of the reactor wall 202. In the coolant film, the velocity of the coolant 218 may be less than the velocity of the bulk coolant flow. The coolant film boundary 222 may generally be taken as the point or surface at which the coolant velocity is at least about 95%, at least about 96%, at least about 97%, at least about 98%, or at least about 99% of the freestream velocity. The coolant film thickness may then be taken as the distance 214 between the exterior surface of the reactor wall 202 and the coolant film boundary 222.

Heat transfer (e.g., convective heat transfer) from the reactor wall 202 through the coolant film layer may be characterized by a coolant film coefficient. The coolant film coefficient characterizes the amount of heat transferred per area, time, and the existing temperature differential (e.g., the temperature gradient) through the coolant film layer. The coolant film coefficient may be determined using any known techniques. An approximation of the coolant film coefficient is provided by Eq. 6.

$$h_{coolant} = 0.058 \cdot \frac{K_C}{D_J} \cdot (Pr_C)^{\frac{1}{2}} \cdot (Re_C)^{0.7} \quad \text{(Eq. 6)}$$

where $h_{coolant}$ is the coolant film coefficient in Btu/(hr)(ft$^2$)(° F.), $K_C$ is the thermal conductivity of the coolant in Btu/(hr)(ft)(F), $D_J$ is the hydraulic diameter of the jacket in (ft), $Pr_c$ is the Prandtl number of the coolant, and $Re_c$ is the Reynolds number of the coolant, where the Prandtl number and the Reynolds number are dimensionless. Various factors may affect the coolant film coefficient. In an embodiment, the coolant velocity, the jacket diameter, the coolant viscosity, the thermal conductivity of the coolant, and various other flow properties of the coolant may affect the calculation of the coolant film coefficient. In an embodiment, the coolant film coefficient may be greater than about 800 BTU·hr$^{-1}$·ft$^{-2}$·° F.$^{-1}$, greater than about 900 BTU·hr$^{-1}$·ft$^{-2}$·° F.$^{-1}$, greater than about 1,000 BTU·hr$^{-1}$·ft$^{-2}$·° F.$^{-1}$, or greater than about 1,100 BTU·hr$^{-1}$·ft$^{-2}$·° F.$^{-1}$. In an embodiment, the slurry film coefficient may be less than about 1,800 BTU·hr$^{-1}$·ft$^{-2}$·° F.$^{-1}$, less than about 1,700 BTU·hr$^{-1}$·ft$^{-2}$·° F.$^{-1}$, or less than about 1,600 BTU·hr$^{-1}$·ft$^{-2}$·° F.$^{-1}$.

The coolant velocity may affect the Reynolds number of the coolant and thereby the coolant film coefficient. In general, an increase in the coolant velocity is expected to result in an increase in the coolant film coefficient, thereby decreasing the resistance to heat transfer through the coolant film. In an embodiment, the coolant velocity within the annulus 218 may be in a range of from about 3 ft/s to about 25 ft/s, or alternatively from about 5 ft/s to about 20 ft/s.

The concept of the Biot number may also be applied to the heat transfer from the reactor wall 202 to the coolant 218, which may be referred to as an external Biot number. The external Biot number represents the balance between the resistance to heat transfer through the reactor wall and the resistance to heat transfer through the coolant film layer. The external Biot number value may provide an indication of the location and magnitude of the greatest resistance to heat transfer, and when used in addition to the internal Biot number may help identify the relative resistances along the entire heat transfer pathway. The external Biot number may be defined using the following equation:

$$B_{ext} = \frac{h_{COOLANT} \cdot L_R}{k_R} \quad \text{(Eq. 7)}$$

where $B_{ext}$ is the external Biot number, $h_{coolant}$ is the coolant film coefficient defined above in units of BTU·hr$^{-1}$·ft$^{-2}$·° F.$^{-1}$, $L_R$ is the characteristic length of the reactor wall (e.g., the thickness 212) in units of ft$^{-1}$, and $k_R$ is the thermal conductivity of the reactor wall in units of BTU·hr$^{-1}$·ft$^{-1}$·° F.$^{-1}$. The external Biot number is referred to as "external" since it represents the relative balance between the resistance to heat transfer through the reactor wall relative to the resistance to heat transfer through the coolant film on the outside of the reactor (e.g., the external heat transfer to the coolant).

A large value of the external Biot number, $B_{ext}$, indicates that the conductive resistance to heat transfer through the reactor wall 202 controls the heat transfer from the loop slurry polymerization reactor 110 relative to the convective heat transfer at the outer surface of the reactor wall 202. Conversely, a small value of the external Biot number indicates that the convective resistance to heat transfer from the reactor wall 202 to the coolant 218 controls the heat transfer from the reactor. In an embodiment, the external Biot number may be maintained at or above about 1.0, at or above about 1.2, at or above about 1.5, at or above about 2.0, or at or above about 3.0 during the reaction process.

Several other ratios may also be useful for operating the polymerization under one or more conditions such that the contribution of the resistance to heat transfer through the slurry film is balanced with respect to the resistances to heat transfer through the reactor wall 202 and/or the coolant film. In an embodiment, the ratio of the slurry film coefficient to the coolant film coefficient ($h_{slurry}$:$h_{coolant}$) may be greater than about 1.5, greater than about 2.0, greater than about 2.5, or greater than about 3.0. A value of the ratio of the slurry film coefficient to the coolant film coefficient above 1.0 may represent that the relative resistance to heat transfer from the reactor wall to the coolant is greater than the relative resistance to heat transfer from the slurry to the reactor wall. Operating the reactor under this condition may ensure that the resistance to heat transfer through the slurry is not the controlling heat transfer resistance in the heat transfer process.

The operating parameters may be useful in designing a polymerization reactor and/or polymerization process. As described herein, the polymerization process may generally comprise polymerizing an olefin monomer, and optionally a comonomer, in a reactor (e.g., loop slurry polymerization reactor 110) in the presence of a catalyst and a diluent. The resulting polymerization reaction may produce solid particulate olefin polymer, which may form a slurry. In order to improve the operation and/or yield of the reactor, the heat transfer pathway may be examined using the operating parameters described herein to determine the relative resistances to heat transfer along the heat transfer pathway between the slurry, reactor wall, and/or the coolant on the exterior of the reactor.

In an embodiment, a reactor design may be based on balancing the contribution of the resistance to heat transfer through the slurry film with the resistances to heat transfer through the reactor wall 202 and/or the coolant film. Using the operating parameters described herein, a reactor composition, a reactor wall thickness, and/or one or more coolant system properties may be determined based on a desired polymerization process. In an embodiment, the operating conditions may be used to determine a reactor wall thickness and/or the reactor wall composition. In this embodiment, the reaction properties including the slurry properties (e.g., solids content, viscosity, flowrate, etc.), the operating temperature, and the like may be used to calculate a slurry film coefficient. The reactor thickness and/or composition may then be selected to conduct the polymerization process where the internal Biot number is maintained at or below about 3.0. In some embodiments, maintaining the Biot number below about 3.0 may be useful with the slurry film coefficient is less than about 500 BTU·hr$^{-1}$·ft$^{-2}$·°F.$^{-1}$ and/or when the slurry has a circulation velocity of greater than about 30 ft/s. Similarly, the reactor thickness and/or composition may be selected to conduct the polymerization process where a ratio of the thermal conductivity to the thickness of the reactor is greater than or equal to about 120 BTU·hr$^{-1}$·ft$^{-2}$·°F.$^{-1}$. In some embodiments, maintaining the ratio of the thermal conductivity to the thickness of the reactor at greater than or equal to about 120 BTU·hr$^{-1}$·ft$^{-2}$·°F.$^{-1}$ may be useful when the volume fraction of the solids in the slurry is greater than about 0.65. In some embodiments, the reactor thickness and/or composition may be selected to conduct the polymerization process where a ratio of the film slurry coefficient to the coolant film coefficient ($h_{slurry}$:$h_{coolant}$) is greater than about 2.0. Any of the additional ratios and/or operating parameters may also be utilized to further constrain the reactor design and/or the coolant system design. The resulting reactor design may allow the reactor to operate within the parameters and/or ratios described herein to effectively remove heat from the reactor during the polymerization process.

In an embodiment, the variables affecting the heat transfer along the heat transfer pathway may be used to determine one or more polymerization operating parameters or conditions in a polymerization reactor system. In an embodiment, the reactor design for an existing loop slurry polymerization reactor 110 may relatively fixed. When the reactor composition and thickness are known (e.g., for an existing loop slurry polymerization reactor 110), the polymerization conditions and/or coolant conditions may be modified to adjust the heat transfer properties of the overall reaction system. For example, the solids content of the reactor, which may affect the slurry film coefficient, may be controlled to maintain the internal Biot number below about 3.0 by controlling the amount of catalyst, diluent, and/or monomer/co-monomer fed to the reactor. Similarly, the velocity of the slurry within the reactor can be modified to maintain the internal Biot number below about 3.0 during the polymerization process. Various other parameters may be determined and/or controlled to provide a reaction system that operates within one or more of the heat transfer characterizations described herein.

The design process may be carried out using a computer comprising a memory and a processor. A computer is described in more detail below. In an embodiment, a method of designing a loop slurry polymerization reactor may begin by simulating a loop slurry polymerization reactor. The simulation may be performed using a simulation program storied in the memory and executed on the processor. The simulator may be configured to model one or more parameters of a loop slurry polymerization reactor. The simulation may generally take into account that the loop slurry polymerization reactor generally comprises at least one loop reactor and at least one cooling jacket disposed about the loop slurry polymerization reactor. As described above, an annulus can be formed between an inner surface of the cooling jacket and an outer surface of a wall of the loop slurry polymerization reactor. In some embodiments, the location of the cooling jacket relative to the loop slurry polymerization reactor can be determined using the simulation.

The simulation may be used to determine a Biot number of a wall region of the loop slurry polymerization reactor. The Biot number may comprise the internal Biot number and/or external Biot number as described herein. Based on the results of the simulating and the calculated Biot numbers, at least one value of at least one design parameter for the loop slurry polymerization reactor can be adjusted. Any of the design parameters described here can be adjusted. In an embodiment, the design parameter for the loop slurry polymerization reactor can include, but is not limited to, a thermal conductivity of the wall of the at least one loop reactor, a diameter of a wall, a thickness of the wall, a velocity of a slurry within the at least one loop reactor, a slurry density of the slurry, a viscosity of the slurry, a specific heat capacity of the slurry, a thermal conductivity of the slurry, a location of the at least one cooling jacket relative to the wall, or any combination thereof.

The simulation can then be repeated using the at least one adjusted value. This process may be repeated any number of iterations until it can be determined that one or more predetermined design parameters are obtained. The predetermined design parameters can include any of the design operating ranges or conditions described herein. In an embodiment, the predetermined design parameter may comprise a wall thickness. This may be useful to provide a desired polymerization process for an existing reactor having a fixed wall thickness. Various other design parameters may also be used as design goals. For example, the design parameter may comprise the internal Biot number, and the design process may obtain the design parameter when the internal Biot number has a value of equal to or less than about 3.0. Similarly, the design parameter can include a film coefficient value for a slurry film formed along the inner wall of the reactor, and the design process may obtain the design parameter when the internal slurry film coefficient is less than about 500 BTU·hr$^{-1}$·ft$^{-2}$·°F.$^{-1}$. The design parameter can comprise a ratio of a thermal conductivity of the reactor wall to the thickness of the reactor wall, and the design process may obtain the design parameter when the ratio of a thermal conductivity of the reactor wall to the thickness of the reactor wall is greater than or equal to about 120 BTU·hr$^{-1}$·ft$^{-2}$·°F.$^{-1}$. In some embodiments, the design parameter can comprise a volume fraction of solids product particles in the slurry. The design process may meet the design parameter when the volume fraction of the solids product particles in the slurry is greater than about 0.65.

Once the desired design parameters are obtained, a loop slurry polymerization reactor design can be output, where the loop slurry polymerization reactor design is based on the simulating, adjusting, repeating, and determining steps. A loop slurry polymerization reactor can then be constructed and operated as described herein.

As part of the design process, a graphical display or output device can be used. In an embodiment, the design process may also include graphically displaying at least a portion of the simulation results. This may aid in identifying one or more of the parameters to be adjusted. The adjusted value of the at least one design parameter can then occur in response to graphically displaying the simulation results.

Figure 4:
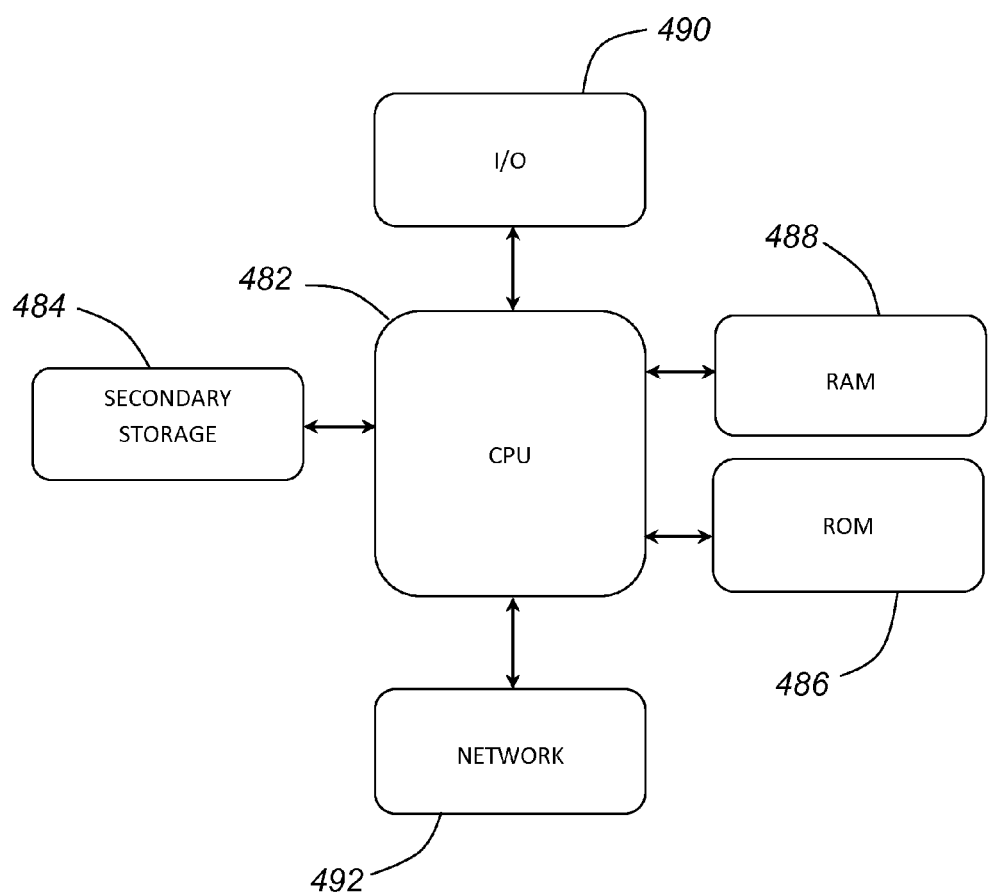
FIG. 4 illustrates a schematic layout of a computer system.

FIG. 4 illustrates a computer system 480 suitable for implementing one or more embodiments disclosed herein. In an embodiment, the computer system 480 may be used to store and/or execute one or more simulation programs used with the polymerization reactor. The computer system 480 includes a processor 482 (which may be referred to as a central processor unit or CPU) that is in communication with memory devices including secondary storage 484, read only memory (ROM) 486, random access memory (RAM) 488, input/output (I/O) devices 490, and network connectivity devices 492. The processor 482 may be implemented as one or more CPU chips.

It is understood that by programming and/or loading executable instructions onto the computer system 480, at least one of the CPU 482, the RAM 488, and the ROM 486 are changed, transforming the computer system 480 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 484 is typically comprised of one or more disk drives or tape drives and is used for non-volatile storage of data and as an over-flow data storage device if RAM 488 is not large enough to hold all working data. Secondary storage 484 may be used to store programs which are loaded into RAM 488 when such programs are selected for execution. The ROM 486 is used to store instructions and perhaps data which are read during program execution. ROM 486 is a non-volatile memory device which typically has a small memory capacity relative to the larger memory capacity of secondary storage 484. The RAM 488 is used to store volatile data and perhaps to store instructions. Access to both ROM 486 and RAM 488 is typically faster than to secondary storage 484. The secondary storage 484, the RAM 488, and/or the ROM 486 may be referred to in some contexts as computer readable storage media and/or non-transitory computer readable media.

I/O devices 490 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 492 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 492 may enable the processor 482 to communicate with the Internet or one or more intranets. With such a network connection, it is contemplated that the processor 482 might receive information from the network, or might output information to the network in the course of performing the above-described method steps. Such information, which is often represented as a sequence of instructions to be executed using processor 482, may be received from and outputted to the network, for example, in the form of a computer data signal embodied in a carrier wave.

Such information, which may include data or instructions to be executed using processor 482 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 482 executes instructions, codes, computer programs, scripts which it accesses from hard disk, floppy disk, optical disk (these various disk based systems may all be considered secondary storage 484), ROM 486, RAM 488, or the network connectivity devices 492. While only one processor 482 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 484, for example, hard drives, floppy disks, optical disks, and/or other device, the ROM 486, and/or the RAM 488 may be referred to in some contexts as non-transitory instructions and/or non-transitory information.

In an embodiment, the computer system 480 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 480 to provide the functionality of a number of servers that is not directly bound to the number of computers in the computer system 480. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 480, at least portions of the contents of the computer program product to the secondary storage 484, to the ROM 486, to the RAM 488, and/or to other non-volatile memory and volatile memory of the computer system 480. The processor 482 may process the executable instructions and/or data structures in part by directly accessing the computer program product, for example by reading from a CD-ROM disk inserted into a disk drive peripheral of the computer system 480. Alternatively, the processor 482 may process the executable instructions and/or data structures by remotely accessing the computer program product, for example by downloading the executable instructions and/or data structures from a remote server through the network connectivity devices 492. The computer program product may comprise instructions that promote the loading and/or copying of data, data structures, files, and/or executable instructions to the secondary storage 484, to the ROM 486, to the RAM 488, and/or to other non-volatile memory and volatile memory of the computer system 480.

In some contexts, the secondary storage 484, the ROM 486, and the RAM 488 may be referred to as a non-transitory computer readable medium or a computer readable storage media. A dynamic RAM embodiment of the RAM 488, likewise, may be referred to as a non-transitory computer readable medium in that while the dynamic RAM receives electrical power and is operated in accordance with its design, for example during a period of time during which the computer system 480 is turned on and operational, the dynamic RAM stores information that is written to it. Similarly, the processor 482 may comprise an internal RAM, an internal ROM, a cache memory, and/or other internal non-transitory storage blocks, sections, or components that may be referred to in some contexts as non-transitory computer readable media or computer readable storage media.

Additional Description

Processes and systems for the balancing the resistances to heat transfer during a polymerization process in a loop polymerization reactor have been described. The following are a first set of nonlimiting, specific embodiments in accordance with the present disclosure:

In a first embodiment, a process comprises polymerizing an olefin monomer in a loop reactor in the presence of a catalyst and a diluent, and producing a slurry comprising solid particulate olefin polymer and diluent. The Biot number is maintained at or below about 3.0 within the loop reactor during the polymerizing. The slurry in the loop reactor forms a slurry film having a film coefficient along an inner surface of the shell, and the film coefficient is less than about 500 $BTU \cdot hr^{-1} \cdot ft^{-2} \cdot °F.^{-1}$.

A second embodiment may include the process of the first embodiment, wherein the Biot number is maintained at or below about 2.0 within the loop reactor during the polymerizing.

A third embodiment may include the process of the first or second embodiment, wherein the Biot number is maintained at or below about 1.5 within the loop reactor during the polymerizing.

A fourth embodiment may include the process of any of the first to third embodiments, wherein the Biot number is maintained at or below about 1.1 within the loop reactor during the polymerizing.

A fifth embodiment may include the process of any of the first to fourth embodiments, wherein the slurry comprises a solids concentration in the range of about 25 wt % to about 70 wt %.

A sixth embodiment may include the process of any of the first to fifth embodiments, wherein the slurry comprises a solids concentration in the range of about 40 wt % to about 60 wt %.

A seventh embodiment may include the process of any of the first to sixth embodiments, wherein the slurry comprises a solids concentration greater than about 50 wt %.

An eighth embodiment may include the process of any of the first to seventh embodiments, wherein the loop reactor comprises a shell having a thickness and a thermal conductivity.

A ninth embodiment may include the process of the eighth embodiment, wherein a ratio of the film coefficient to the thermal conductivity is in a range of from about 8.0 $ft^{-1}$ to about 50 $ft^{-1}$.

A tenth embodiment may include the process of the eighth or ninth embodiment, wherein a ratio of the film coefficient to the thermal conductivity is in a range of from about 14 $ft^{-1}$ to about 35 $ft^{-1}$.

An eleventh embodiment may include the process of any of the eighth to tenth embodiments, wherein a ratio of the film coefficient to the thickness is in a range of from about 1,400 $BTU \cdot hr^{-1} \cdot ft^{-3} \cdot °F.^{-1}$ to about 240,000 $BTU \cdot hr^{-1} \cdot ft^{-3} \cdot °F.^{-1}$.

A twelfth embodiment may include the process of any of the eighth to eleventh embodiments, wherein a ratio of the film coefficient to the thickness is in a range of from about 2,400 BTU·hr$^{-1}$·ft$^{-3}$·°F.$^{-1}$ to about 100,000 BTU·hr$^{-1}$·ft$^{-3}$·°F.$^{-1}$.

A thirteenth embodiment may include the process of any of the eighth to twelfth embodiments, wherein a ratio of the thermal conductivity to the thickness is in a range of from about 100 BTU·hr$^{-1}$·ft$^{-2}$·°F.$^{-1}$ to about 10,000 BTU·hr$^{-1}$·ft$^{-2}$·°F.$^{-1}$.

A fourteenth embodiment may include the process of any of the eighth to thirteenth embodiments, wherein a ratio of the thermal conductivity to the thickness is in a range of from about 120 BTU·hr$^{-1}$·ft$^{-2}$·°F.$^{-1}$ to about 4,000 BTU·hr$^{-1}$·ft$^{-2}$·°F.$^{-1}$.

A fifteenth embodiment may include the process of any of the eighth to fourteenth embodiments, wherein the shell comprises a steel selected from the group consisting of: A106 Gr 8 (60), A516 Gr 70, A537 Cl 2, A106 Gr C (40), A202 Gr 8, A285 Gr C, A514 Gr 8, A515 Gr 70, A517 Gr A, A517 Gr 8, A533 Ty A C13, A542 Ty A C12, A678 Gr C, AISI 1010, AISI 1015, MIL-S 24645, and any combination thereof.

A sixteenth embodiment may include the process of any of the eighth to fifteenth embodiments, wherein the shell has a diameter in the range of about 20 inches to about 36 inches.

A seventeenth embodiment may include the process of any of the eighth to sixteenth embodiments, wherein the inner surface of the shell has a surface smoothness of less than 100 RMS microinches.

An eighteenth embodiment may include the process of any of the eighth to seventeenth embodiments, wherein the inner surface of the shell has a surface smoothness of less than 30 RMS microinches.

A nineteenth embodiment may include the process of any of the eighth to eighteenth embodiments, wherein the inner surface of the shell has a surface smoothness of between about 10 RMS microinches and about 30 RMS microinches.

A twentieth embodiment may include the process of any of the first to nineteenth embodiments, where the method may also include circulating the slurry within the loop reactor, and wherein the slurry is circulated at a velocity in the range of about 25 ft/s to about 60 ft/s.

A twenty first embodiment may include the process of any of the first to twentieth embodiments, where the process may also include circulating the slurry within the loop reactor, and wherein the slurry is circulated at a velocity in the range of about 35 ft/s to about 50 ft/s.

A twenty second embodiment may include the process of any of the first to twenty first embodiments, where the process may also include circulating the slurry within the loop reactor, and wherein the slurry is circulated at a velocity greater than about 40 ft/s.

In a twenty third embodiment, a reactor comprises a continuous tubular shell comprising a thickness and a thermal conductivity, and a slurry disposed within the continuous tubular shell. The continuous tubular shell defines a continuous loop and a ratio of the thermal conductivity to the thickness is greater than or equal to about 120 BTU·hr$^{-1}$·ft$^{-2}$·°F.$^{-1}$. The slurry comprises solid particulate olefin polymer and a diluent, and the volume fraction of the solids in the slurry is greater than about 0.65.

A twenty fourth embodiment may include the reactor of the twenty third embodiment, wherein the ratio of the thermal conductivity to the thickness is greater than or equal to about 160 BTU·hr$^{-1}$·ft$^{-2}$·°F.$^{-1}$.

A twenty fifth embodiment may include the reactor of the twenty third or twenty fourth embodiment, wherein the ratio of the thermal conductivity to the thickness is greater than or equal to about 250 BTU·hr$^{-1}$·ft$^{-2}$·°F.$^{-1}$.

A twenty sixth embodiment may include the reactor of any of the twenty third to twenty fifth embodiments, wherein the ratio of the thermal conductivity to the thickness is greater than or equal to about 300 BTU·hr$^{-1}$·ft$^{-2}$·°F.$^{-1}$.

A twenty seventh embodiment may include the reactor of any of the twenty third to twenty sixth embodiments, wherein the thermal conductivity of the shell is between about 20 and about 40 BTU·hr$^{-1}$·ft$^{-2}$·°F.$^{-1}$.

A twenty eighth embodiment may include the reactor of any of the twenty third to twenty seventh embodiments, wherein the shell comprises a steel selected from the group consisting of: A106 Gr 8 (60), A516 Gr 70, A537 Cl 2, A106 Gr C (40), A202 Gr 8, A285 Gr C, A514 Gr 8, A515 Gr 70, A517 Gr A, A517 Gr 8, A533 Ty A C13, A542 Ty A C12, A678 Gr C, AISI 1010, AISI 1015, MIL-S 24645, and any combination thereof.

A twenty ninth embodiment may include the reactor of any of the twenty third to twenty eighth embodiments, wherein the shell comprises a steel comprising iron and one or more of components selected from the group consisting of: carbon in an amount of from about 0.05 wt % to about 0.25 wt %, silicon in an amount of from about 0.5 wt % to about 0.75 wt %, manganese in an amount of from about 0.8 wt % to about 2.0 wt %, phosphorous in an amount of from about 0.01 wt % to about 0.1 wt %, sulfur in an amount of from about 0.01 wt % to about 0.1 wt %, aluminum in an amount of from about 0.01 wt % to about 0.04 wt %, chromium in an amount of from about 0.1 wt % to about 0.5 wt %, copper in an amount of from about 0.1 wt % to about 0.5 wt %, nickel in an amount of from about 0.1 wt % to about 0.5 wt %, molybdenum in an amount of from about 0.05 wt % to about 0.1 wt %, niobium in an amount of from about 0.005 wt % to about 0.02 wt %, titanium in an amount of from about 0.01 wt % to about 0.05 wt %, vanadium in an amount of from about 0.01 wt % to about 0.04 wt %, and any combination thereof.

In a thirtieth embodiment, a process comprises polymerizing an olefin monomer in a loop reactor in the presence of a catalyst and a diluent, where the loop reactor comprises a continuous tubular shell, producing a slurry comprising solid particulate olefin polymer and diluent, and circulating the slurry in the loop reactor. The slurry in the loop reactor forms a slurry film along an inner surface of the shell, and a ratio of a heat transfer resistance through the slurry film to a heat transfer resistance through the tubular shell is maintained at or below about 3.0 within the loop reactor during the polymerizing. The slurry has a velocity of greater than about 30 ft/s during the circulating.

A thirty first embodiment may include the process of the thirtieth embodiment, wherein the ratio of the heat transfer resistance through the slurry film to the heat transfer resistance through the tubular shell is maintained at or below about 2.0 within the loop reactor during the polymerizing.

A thirty second embodiment may include the process of the thirtieth or thirty first embodiment, wherein the ratio of the heat transfer resistance through the slurry film to the heat transfer resistance through the tubular shell is maintained at or below about 1.5 within the loop reactor during the polymerizing.

A thirty third embodiment may include the process of any of the thirtieth to thirty second embodiments, wherein the slurry comprises a solids concentration in the range of about 25 wt % to about 70 wt %.

A thirty fourth embodiment may include the process of any of the thirtieth to thirty third embodiments, wherein the slurry comprises a solids volume fraction above about 0.65.

A thirty fifth embodiment may include the process of any of the thirtieth to thirty fourth embodiments, wherein the slurry is circulated at a velocity greater than about 40 ft/s.

A thirty sixth embodiment may include the process of any of the thirtieth to thirty fifth embodiments, wherein the slurry is circulated at a velocity greater than about 50 ft/s.

In a thirty seventh embodiment, a polymerization process comprises polymerizing an olefin monomer in a loop reactor in the presence of a catalyst and a diluent, producing a slurry comprising solid particulate olefin polymer and diluent within the loop reactor, and contacting at least a portion of an exterior surface of the loop reactor with a coolant fluid. The slurry in the loop reactor forms a slurry film having a film coefficient along an inner surface of the loop reactor, and the coolant fluid forms a coolant film having a coolant film coefficient along an exterior surface of the loop reactor. A ratio of the film coefficient to the coolant film coefficient is greater than about 2.0.

A thirty eighth embodiment may include the polymerization process of the thirty seventh embodiment, wherein an external Biot number is greater than about 2.0 during the polymerizing.

A thirty ninth embodiment may include the polymerization process of the thirty seventh or thirty eighth embodiment, wherein an internal Biot number is less than about 3.0 during the polymerizing.

A fortieth embodiment may include the polymerization process of any of the thirty seventh to thirty ninth embodiments, wherein the slurry comprises a solids volume fraction above about 0.65.

A forty first embodiment may include the polymerization process of any of the thirty seventh to fortieth embodiments, where the polymerization process may also include circulating the slurry in the loop reactor, and wherein the slurry has a velocity of greater than about 30 ft/s during the circulating.

In a forty second embodiment, a method of designing a loop slurry polymerization reactor comprises simulating, on a processor, a loop slurry polymerization reactor, determining a Biot number of a shell region of the at least one loop slurry polymerization reactor based on the simulating, adjusting a value of at least one design parameter for the loop slurry polymerization reactor based on the simulating, repeating the simulating, by the processor, based on the adjusted value of the at least one design parameter, determining that one or more predetermined design parameters are obtained based on the repeating, and outputting a loop slurry polymerization reactor design based on the simulating, adjusting, repeating, and determining. The loop slurry polymerization reactor comprises at least one loop reactor and at least one cooling jacket, and an annulus exists between a wall of the at least one loop reactor and the cooling jacket.

A forty third embodiment may include the method of the forty second embodiment, further comprising: graphically displaying at least a portion of the simulating, and adjusting the value of the at least one design parameter in response to the graphically displaying.

A forty fourth embodiment may include the method of the forty second or forty third embodiment, further comprising: determining a position of the at least one cooling jacket adjacent and substantially parallel to at least a portion of a leg of the at least one loop reactor.

A forty fifth embodiment may include the method of any of the forty second to forty fourth embodiments, wherein the at least one design parameter for the loop slurry polymerization reactor comprises a thermal conductivity of the wall of the at least one loop reactor, a diameter of a wall, a thickness of the wall, a velocity of a slurry within the at least one loop reactor, a slurry density of the slurry, a viscosity of the slurry, a specific heat capacity of the slurry, a thermal conductivity of the slurry, a location of the at least one cooling jacket relative to the wall, or any combination thereof.

A forty sixth embodiment may include the method of any of the forty second to forty fifth embodiments, wherein the one or more predetermined design parameters comprises a wall thickness.

A forty seventh embodiment may include the method of any of the forty second to forty sixth embodiments, wherein the one or more predetermined design parameters comprises an internal Biot number equal to or less than about 3.0.

A forty eighth embodiment may include the method of any of the forty second to forty seventh embodiments, wherein a slurry in the at least one loop reactor forms a slurry film having a film coefficient along an inner surface of a wall of the at least one loop reactor, and wherein the one or more predetermined design parameters comprises the film coefficient of less than about 500 BTU·$hr^{-1}$·$ft^{-2}$·°$F.^{-1}$.

A forty ninth embodiment may include the method of any of the forty second to forty eighth embodiments, wherein a wall of the at least one loop reactor comprises a thickness and a thermal conductivity, and wherein the one or more predetermined design parameters comprises a ratio of the thermal conductivity to the thickness that is greater than or equal to about 120 BTU·$hr^{-1}$·$ft^{-2}$·°$F.^{-1}$.

A fiftieth embodiment may include the method of any of the forty second to forty ninth embodiments, wherein the at least one loop reactor comprises a slurry disposed within a wall of the at least one loop reactor, wherein the slurry comprises solid particulate olefin polymer and a diluent, and wherein the one or more predetermined design parameters comprises a volume fraction of the solid particulate olefin polymer in the slurry that is greater than about 0.65.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the disclosure is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A process comprising:
   polymerizing an olefin monomer in a loop reactor in the presence of a catalyst and a diluent; and
   producing a slurry comprising solid particulate olefin polymer and diluent, wherein the Biot number is maintained at or below 3.0 within the loop reactor during the polymerizing, wherein the slurry in the loop reactor forms a slurry film having a film coefficient along an inner surface of a reactor wall, and wherein the film coefficient is less than 500 BTU·hr$^{-1}$·ft$^{-2}$·°F.$^{-1}$.

2. The process of claim 1, wherein the slurry comprises a solids concentration in the range of about 25 wt % to about 70 wt %.

3. The process of claim 1, wherein the slurry comprises a solids concentration greater than about 50 wt %.

4. The process of claim 1, wherein the loop reactor comprises a reactor wall having a thickness and a thermal conductivity.

5. The process of claim 4, wherein a ratio of the film coefficient to the thermal conductivity is in a range of from about 8.0 ft$^{-1}$ to about 50 ft$^{-1}$.

6. The process of claim 4, wherein a ratio of the film coefficient to the thickness is in a range of from about 1,400 BTU·hr$^{-1}$·ft$^{-3}$·°F.$^{-1}$ to about 240,000 BTU·hr$^{-1}$·ft$^{-3}$·°F.$^{-1}$.

7. The process of claim 4, wherein a ratio of the thermal conductivity to the thickness is in a range of from about 100 BTU·hr$^{-1}$·ft$^{-2}$·°F.$^{-1}$ to about 10,000 BTU·hr$^{-1}$·ft$^{-2}$·°F.$^{-1}$.

8. The process of claim 4, wherein the reactor wall comprises a steel selected from the group consisting of: A106 Gr 8 (60), A516 Gr 70, A537 Cl 2, A106 Gr C (40), A202 Gr 8, A285 Gr C, A514 Gr 8, A515 Gr 70, A517 Gr A, A517 Gr 8, A533 Ty A C13, A542 Ty A C12, A678 Gr C, AISI 1010, AISI 1015, MIL-S 24645, and any combination thereof.

9. The process of claim 4, wherein the reactor wall has a diameter in the range of about 20 inches to about 36 inches.

10. The process of claim 4, wherein the inner surface of the reactor wall has a surface smoothness of less than 30 RMS microinches.

11. The process of claim 1, further comprising: circulating the slurry within the loop reactor, wherein the slurry is circulated at a velocity in the range of about 25 ft/s to about 60 ft/s.

12. The process of claim 1, further comprising: circulating the slurry within the loop reactor, wherein the slurry is circulated at a velocity greater than 40 ft/s.

13. A process comprising:
    polymerizing an olefin monomer in a loop reactor in the presence of a catalyst and a diluent, wherein the loop reactor comprises a continuous tubular shell;
    producing a slurry comprising solid particulate olefin polymer and diluent, wherein the slurry in the loop reactor forms a slurry film along an inner surface of the shell, and wherein a ratio of a heat transfer resistance through the slurry film to a heat transfer resistance through the tubular shell is maintained at or below 3.0 within the loop reactor during the polymerizing; and
    circulating the slurry in the loop reactor, wherein the slurry has a velocity of greater than 30 ft/s during the circulating.

14. The process of claim 13, wherein the ratio of the heat transfer resistance through the slurry film to the heat transfer resistance through the tubular shell is maintained at or below 2.0 within the loop reactor during the polymerizing.

15. The process of claim 13, wherein the slurry comprises a solids concentration in the range of about 25 wt % to about 70 wt %.

16. The process of claim 13, wherein the slurry comprises a solids volume fraction above 0.65.

* * * * *